United States Patent
Einarsson et al.

(10) Patent No.: US 12,167,954 B2
(45) Date of Patent: Dec. 17, 2024

(54) SYSTEMS AND METHODS FOR TREATING STRESS URINARY INCONTINENCE

(71) Applicants: The Brigham and Women's Hospital, Inc., Boston, MA (US); Freyja Healthcare, LLC, North Andover, MA (US)

(72) Inventors: Jon I. Einarsson, Boston, MA (US); James Bleck, North Andover, MA (US); John Aho, North Andover, MA (US); Jonathan Towle, North Andover, MA (US)

(73) Assignees: Freyja Healthcare, LLC, North Andover, MA (US); The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 18/060,354

(22) Filed: Nov. 30, 2022

(65) Prior Publication Data
US 2023/0165668 A1 Jun. 1, 2023

Related U.S. Application Data

(63) Continuation of application No. PCT/US2021/040010, filed on Jun. 30, 2021.
(Continued)

(51) Int. Cl.
*A61F 2/00* (2006.01)
*A61B 17/00* (2006.01)
(Continued)

(52) U.S. Cl.
CPC .. *A61F 2/0045* (2013.01); *A61B 2017/00805* (2013.01); *A61B 2017/0409* (2013.01); *A61B 2017/06176* (2013.01)

(58) Field of Classification Search
CPC ........... A61F 2/0045; A61F 2250/0031; A61B 2017/00805; A61B 2017/0409;
(Continued)

(56) References Cited

U.S. PATENT DOCUMENTS 10,398,431 B2  9/2019 Mujwid et al.
2006/0201519 A1  9/2006 Frazier et al.
(Continued)

FOREIGN PATENT DOCUMENTS

WO  2022006350 A1  1/2022

OTHER PUBLICATIONS

International Search Report dated Dec. 16, 2022 for International Application No. PCT/US2021/040010.
(Continued)

*Primary Examiner* — Sunita Reddy
(74) *Attorney, Agent, or Firm* — DeWitt LLP; Brian R. Pollack, Esq.

(57) ABSTRACT

The disclosure provides improved methods and devices to create a hammock effect to stabilize the urethra without creating an incision in the abdomen or the vagina, and without using a surgical mesh. Such implementations can also leave no permanent material in the body. The simplicity afforded by such procedures and methods permits treatment of patients on an outpatient basis, and avoids risks and disadvantages associated with the installation of a permanent mesh.

17 Claims, 43 Drawing Sheets

Related U.S. Application Data

(60) Provisional application No. 63/045,918, filed on Jun. 30, 2020.

(51) Int. Cl.
 *A61B 17/04* (2006.01)
 *A61B 17/06* (2006.01)

(58) Field of Classification Search
 CPC ...... A61B 2017/06176; A61B 17/0401; A61B 2017/0417; A61B 2017/0464; A61B 17/0487; A61B 17/06166; A61B 17/06109
 USPC ...................................................... 600/29–32
 See application file for complete search history.

(56) References Cited

U.S. PATENT DOCUMENTS

| | | | |
|---|---|---|---|
| 2009/0137862 A1 | 5/2009 | Evans et al. | |
| 2013/0023724 A1* | 1/2013 | Allen | A61B 17/0401 |
| | | | 600/30 |
| 2013/0023906 A1* | 1/2013 | Kubalak | A61B 17/0482 |
| | | | 606/144 |
| 2014/0025112 A1* | 1/2014 | Bonutti | A61B 17/0487 |
| | | | 606/232 |
| 2014/0031835 A1* | 1/2014 | Viker | A61B 17/3468 |
| | | | 606/151 |
| 2016/0038267 A1* | 2/2016 | Allen | A61F 2/0004 |
| | | | 606/232 |
| 2016/0324615 A1 | 11/2016 | Lund et al. | |
| 2017/0340329 A1* | 11/2017 | Groothuis | A61B 17/0401 |
| 2019/0117211 A1 | 4/2019 | Catanese et al. | |
| 2019/0160332 A1 | 5/2019 | Beer et al. | |
| 2019/0254799 A1 | 8/2019 | Lamson et al. | |
| 2019/0254801 A1* | 8/2019 | Lund | A61F 2/0036 |

OTHER PUBLICATIONS

Written Opinion of the International Searching Authority dated Dec. 16, 2022 for International Application No. PCT/US2021/040010.
Supplementary European Search Report for Application No. 21831648.7, dated Jun. 21, 2024, 10 pages.

* cited by examiner

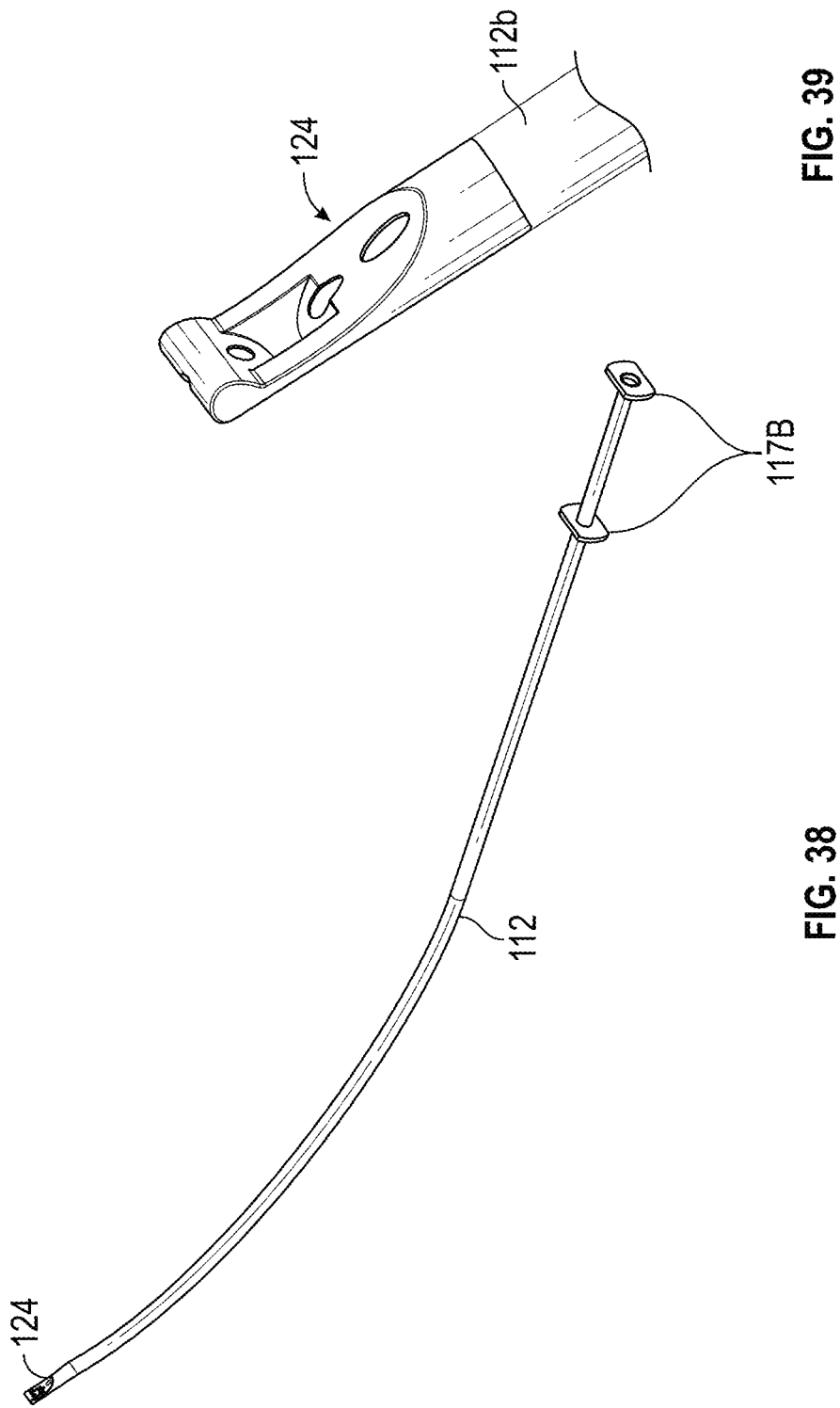

SYSTEMS AND METHODS FOR TREATING STRESS URINARY INCONTINENCE

CROSS-REFERENCE TO RELATED APPLICATIONS

The present patent application is a continuation of International Patent Application No. PCT/US2021/040010, filed Jun. 30, 2021 (published as WO2022006350A1), which in turn claims the benefit of priority to U.S. Provisional Patent Application Ser. No. 63/045,918, filed Jun. 30, 2020. Each of the aforementioned patent applications is incorporated by reference herein in its entirety for all purposes.

BACKGROUND

Stress urinary incontinence (SUI) affects around 15-60% of women during their lifetime. Urine leakage happens when the person laughs, coughs, sneezes, lifts things, or during exercise. The current standard of care for surgical treatment of stress urinary incontinence (SUI) is the polypropylene mesh vaginal sling procedure. This has the highest efficacy as well as the highest improvement in quality of life of any SUI procedure. However, polypropylene mesh has recently come under severe scrutiny due to risks such as infection and erosion, and the use of vaginal mesh has been largely abandoned for the surgical treatment of pelvic organ prolapse. Its use continues for the treatment of SUI, but there is increasing concern over the long term safety of this approach and there are many ongoing product liability lawsuits pertaining to these issues. A few countries, such as Scotland, have banned all pelvic mesh procedures, including the use of SUI mesh slings. There are alternatives to slings, the most common being the Burch procedure, wherein sutures are placed along the urethra, either through an open incision or laparoscopically. The open incision surgery is associated with high morbidity and hospital stay, and the laparoscopic placement is very technically difficult to perform. FIG. 1 shows the difference between the Burch procedure and the autologous sling procedure.

In the Burch procedure (FIG. 1A), the anterior vaginal wall is suspended at the level of the bladder neck with sutures tied to the Cooper's (iliopectineal) ligament. As illustrated, two sutures are placed on either side of the anterior vaginal wall, wherein one is placed at the bladder neck and the other is placed at the midurethra. These pairs of sutures are then tied up to the Cooper's (iliopectineal) ligament thereby suspending the anterior vaginal wall, thereby creating a hammock effect on the urethra. The resulting increased stability of the urethra prevents urine from leaking out during cough or strenuous activity.

The autologous sling procedure is illustrated in FIG. 1B. In this procedure, a harvested strip of rectus fascia is placed transvaginally at the level of the proximal urethra. The fascial strip is secured superiorly to the rectus fascia (rectus abdominus muscle) with permanent sutures. This forms a sling underneath the urethra close to the bladder neck. This in turn helps to elevate and stabilize the bladder neck and the urethra.

In the past, there were also needle procedures that used permanent sutures that were passed with a needle through the vagina and through the rectus fascia and the sutures were used to create a hammock under the urethra and thereby stabilizing it. However, these procedures required an incision in the vagina as well as abdominal incisions and were therefore mostly abandoned when the simpler sling procedure arrived. But, these needle procedures were nonetheless fairly effective to treat SUI. One such procedure is known as the Pereyra procedure. In this technique, a loop of suture or other material is inserted through the paraurethral tissue near the bladder neck and is attached to the abdominal fascia to elevate the bladder. Needles are used to pass suture material from the vagina and through the abdominal wall. These needles are sometimes directed trough the vagina first and then under the pubic bone and through the skin or they can be placed in the reverse order. FIG. 2 illustrates how the needle passes through the vagina lateral to the urethra close to the bladder neck (junction between urethra and bladder). It also passes behind the pubic bone and penetrates the rectus fascia and the skin. As will be appreciated, there is room for improvement in the art to improve upon the techniques discussed above.

SUMMARY OF THE DISCLOSURE

Advantages of the present disclosure will be set forth in and become apparent from the description that follows. Additional advantages of the disclosure will be realized and attained by the methods and systems particularly pointed out in the written description and claims hereof, as well as from the appended drawings.

In accordance with some implementations, the disclosure provides methods and devices for treating stress urinary incontinence (SUI).

In accordance with some implementations, a system for treating stress urinary incontinence (SUI) is provided, including a housing including at least one actuator, an elongate shaft extending distally from the actuator, a tissue anchor disposed at a distal end of the elongate shaft, a tether coupled to the tissue anchor, and an actuator disposed in the housing to release the tissue anchor after the tissue anchor has been disposed in tissue, wherein the elongate shaft can be removed after the tissue anchor has been released to leave behind the tissue anchor and the tether.

In some implementations, the system can further include at least one pull wire coupled to the actuator and to the tissue anchor, wherein pulling the at least one pull wire by way of the actuator causes the tissue anchor to separate from the elongate shaft. The system can further include at least one push rod coupled to a further actuator, wherein the at least one push rod is configured to be advanced distally to change the orientation of the tissue anchor after the tissue anchor has been separated from the elongate shaft. The elongate shaft can define at least one lumen along its length. Each of the pull wire and the push rod can traverse at least part of the length of the elongate shaft from the housing to the tissue anchor. In some embodiments, the tissue anchor can form a leading end of the system and includes a tissue dissection tip. In some implementations, the tether can pass through an opening defined in the anchor. The first and second ends of the tether can be coupled to the housing.

In accordance with further implementations, the system can further include a vaginal anchor to be coupled to the tether. The vaginal anchor can be configured to couple to the tether after tension has been applied to the tether after the tissue anchor has been implanted. The vaginal anchor can include at least one cleat to couple to the tether. In some implementations, the vaginal anchor can include two housing components that couple together. The two housing components can clamp against the tether when the housing components are coupled together. In some implementations, the two housing components can couple in a plurality of positions.

In some implementations, the fascial anchor can be disposed within the shaft prior to being deployed. If desired, the tissue anchor can form at least one of an X-shape, a star shape, a disc shape and an elongate shape after it is deployed. At least one of the fascial anchor, the vaginal anchor and the tether can be formed at least in part from bioresorbable material. The bioresorbable material includes PDS, for example. The vaginal anchor can be defined by a smooth and oblong surface.

In accordance with further aspects, the disclosure further provides implementations of methods of treating stress urinary incontinence (SUI).

In some implementations, the method can include delivering a tether along a first pathway from a location inside the vagina to a location proximate to the rectus abdominus, wherein the first pathway is laterally offset from the urethra, deploying a fascial anchor anterior to the rectus abdominus attached to a first end of the tether, coupling a vaginal anchor to a second end of the tether inside the vaginal canal, and applying tension to the tether and raising the vaginal anchor to lift the anterior wall of the vaginal canal.

If desired, in some implementations, delivering the tether can include introducing an elongate shaft along the pathway. The fascial anchor can be coupled to the elongate shaft prior to being deployed. The elongate shaft can be introduced through the vaginal opening, through the vaginal wall along the pathway, and through the rectus abdominus. The fascial anchor can be deployed after at least a portion of the elongate shaft has traversed the rectus abdominus. The method can further include removing the elongate shaft through the vaginal canal and loading the vaginal anchor onto the tether during the coupling step. The method can further include delivering a second tether along a second pathway near the first pathway. At least one of the first pathway and second pathway can pass near the mid-urethra. The other of the first pathway and second pathway can pass near the bladder neck. In some embodiments, a first tether can be connected to a first vaginal anchor inside the vaginal canal, and a second tether can be connected to a second vaginal anchor inside the vaginal canal.

In some implementations, the method can further include adjusting relative placement of the vaginal anchor and the tether after the procedure. The adjusting step can include un-securing the tether and loosening the vaginal anchor. In some implementations, the adjusting step can include un-securing the tether and tightening the vaginal anchor.

In some implementations, the disclosure provides methods of treating stress urinary incontinence (SUI) including delivering a tether along a first pathway from a location inside the vagina to a location proximate to the obturator internus muscle, deploying an anchor coupled to a first end region of the tether into the obturator internus muscle, coupling a vaginal anchor to a second end of the tether inside the vaginal canal, and applying tension to the tether and raising the vaginal anchor to lift the anterior wall of the vaginal canal.

In some aspects, the anchor can include at least one barb integral with the suture. In other aspects, the anchor can include at least one deployable anchor coupled to a first end of the tether.

The disclosure further provides a method of treating stress urinary incontinence (SUI) that includes delivering a barbed tether along a first pathway from a location inside the vagina to a location proximate to the rectus abdominus, wherein the first pathway is laterally offset from the urethra, disposing at least some of the barbs of the barbed tether into the rectus abdominus attached to a first end region of the tether, coupling a vaginal anchor to a second end of the tether inside the vaginal canal, and applying tension to the tether and raising the vaginal anchor to lift the anterior wall of the vaginal canal.

In further accordance with the disclosure, any system as described herein can further include matrix material to induce scarring in the region of the procedure. The matrix material can be coupled to the tether. The matrix material can be made at least in part from a bioresorbable material. The bioresorbable material can include at least one of Poly polydioxanone (PDS), Poly (lactic acid), Poly D Lactic Acid, and Poly L Lactic Acid. The matrix material can be integrally formed with the tether.

In further accordance with the disclosure, any method as described herein can further include delivering matrix material along the first pathway to induce scarring in the region of the procedure. The matrix material can be coupled to the tether and pulled into the first pathway due to being coupled to the tether. The matrix material can be introduced in a separate step from introducing the tether.

It is to be understood that the foregoing general description and the following detailed description are exemplary and are intended to provide further explanation of the disclosed embodiments. The accompanying drawings, which are incorporated in and constitute part of this specification, are included to illustrate and provide a further understanding of the disclosed methods and systems. Together with the description, the drawings serve to explain principles of the disclosure.

BRIEF DESCRIPTION OF THE DRAWINGS

The accompanying drawings illustrate various example, non-limiting, inventive aspects, embodiments, and features ("e.g.," or "example(s)") in accordance with the present disclosure:

FIGS. 38-39 are isometric views of portions of the system of FIG. 14.

DESCRIPTION

The purpose and advantages of embodiments of the present disclosure will be set forth in and become apparent from the description that follows. Additional advantages of embodiments of the present disclosure will be realized and attained by the methods and systems particularly pointed out in the written description and claims hereof, as well as from the appended drawings.

In some implementations, the disclosure provides improved methods and devices to create a hammock effect to stabilize the urethra without creating an incision in the abdomen or the vagina, and without using a surgical mesh. Such implementations also leave no permanent material in the body. The simplicity afforded by such procedures and methods permits treatment of patients on an outpatient basis, and avoids risks and disadvantages associated with the installation of a permanent mesh. Moreover, in some implementations, the system and method permit adjustment of the system during an outpatient visit if it is determined that the system was initially implanted in a manner that is too tight or too loose. This can easily be contrasted with a conventional mesh sling procedure. If a mesh sling is placed too tight, the mesh has to be removed by way of a major surgical procedure. If a mesh sling is placed too loosely, it cannot be easily adjusted and it is less effective.

In some implementations, a system is provided that includes a small diameter (e.g, 1-2 mm) needle that carries within it a folded fascial anchor to anchor in fascia coupled to a first end of a thread (e.g, suture, tether, or the like). If desired, the suture can include a barbed suture, or a suture with a barbed portion that is directed through the fascia and the barbs can prevent the suture from backing out. An anchor can be used in combination with a partially or fully barbed suture, such as but not limited to a molded barbed suture. In some embodiments, the thread, suture, and/or anchor can be made from a resorbable material such as polydioxanone (PDS). PDS is a delayed absorbable material that generally dissolves completely within 6 months of implantation. In some implementations, the device can also include a vaginal anchor to be coupled to a second end of the thread to urge against the vaginal wall. The vaginal anchor can be provided with one or more smooth surfaces to minimize its physical profile in the vaginal canal. The vaginal anchor can also me made from a bioresorbable material such as PDS.

Figure 1A:
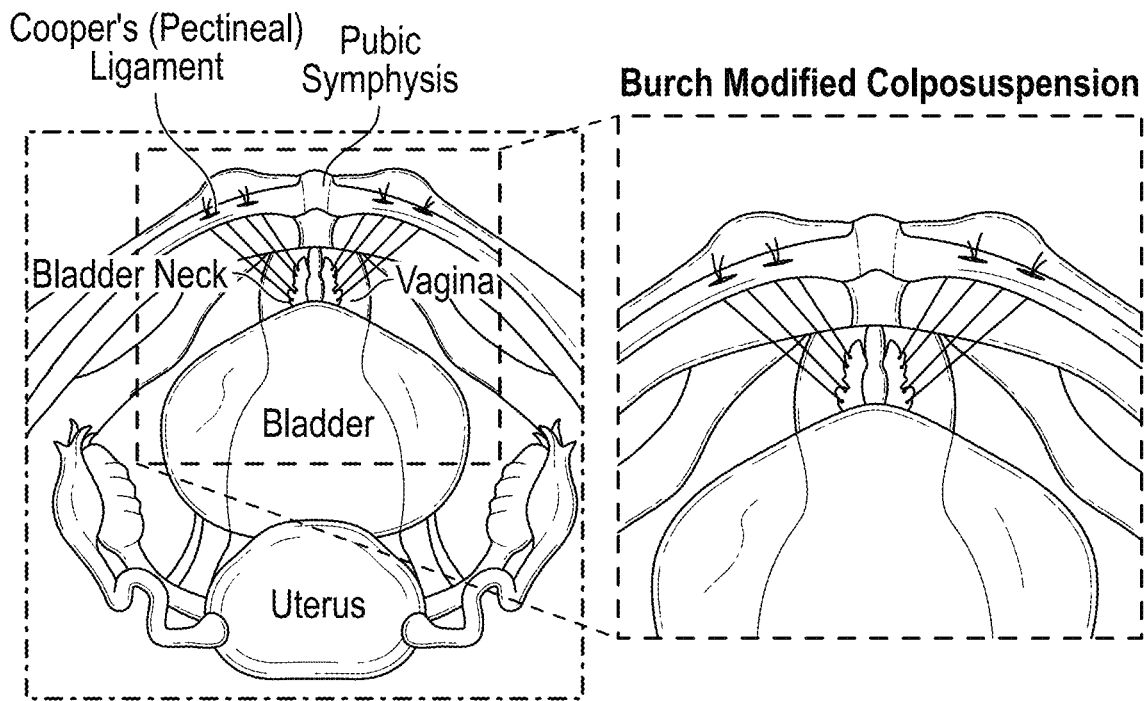
FIG. 1A illustrates an example of a Burch procedure, as is known in the art.
Figure 1B:
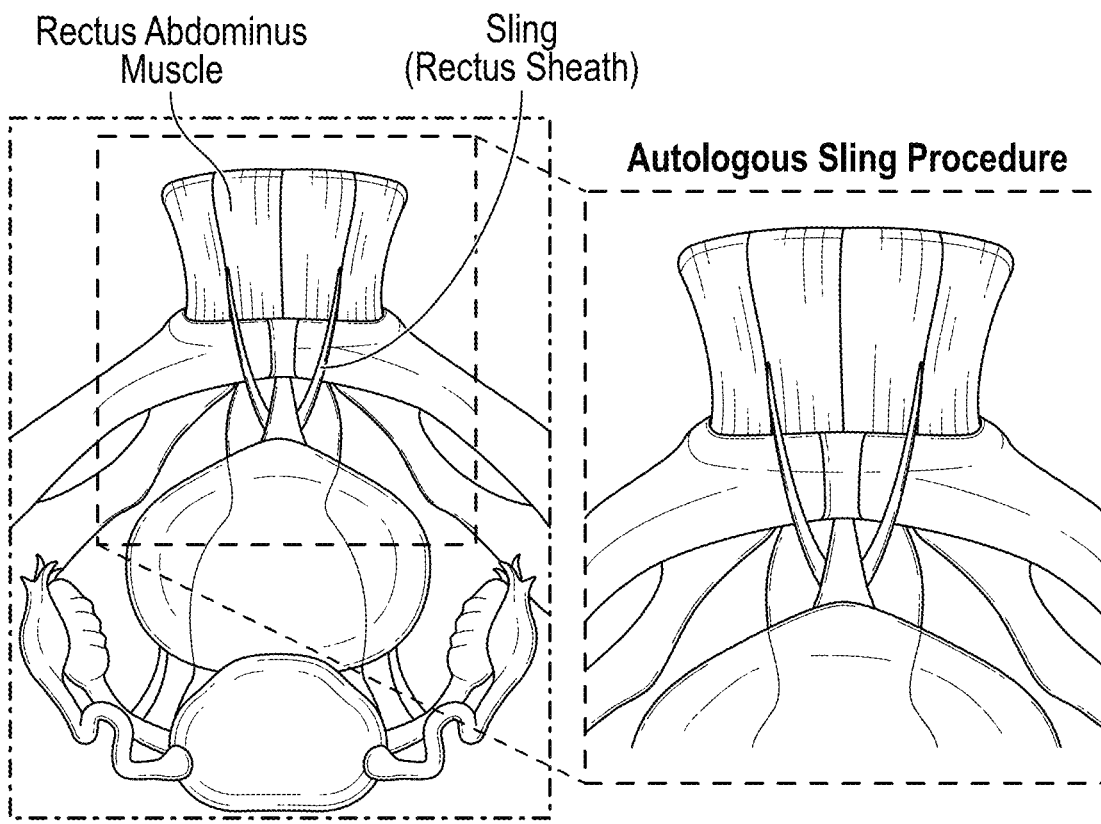
FIG. 1B illustrates an example of an autologous sling procedure, as is known in the art.
Figure 2:
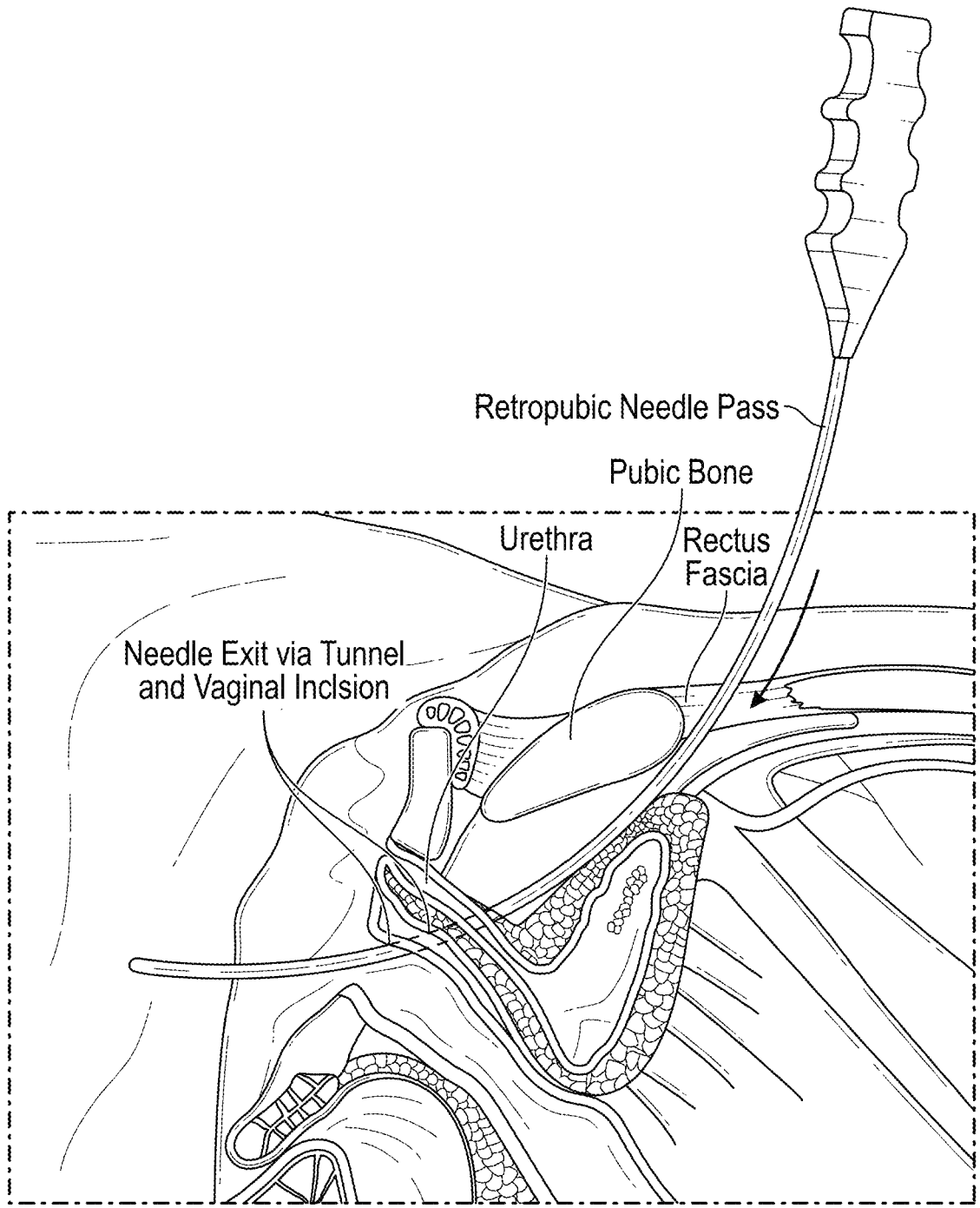
FIG. 2 illustrates an aspect of a Pereyra procedure, as is known in the art.
Figure 3A:
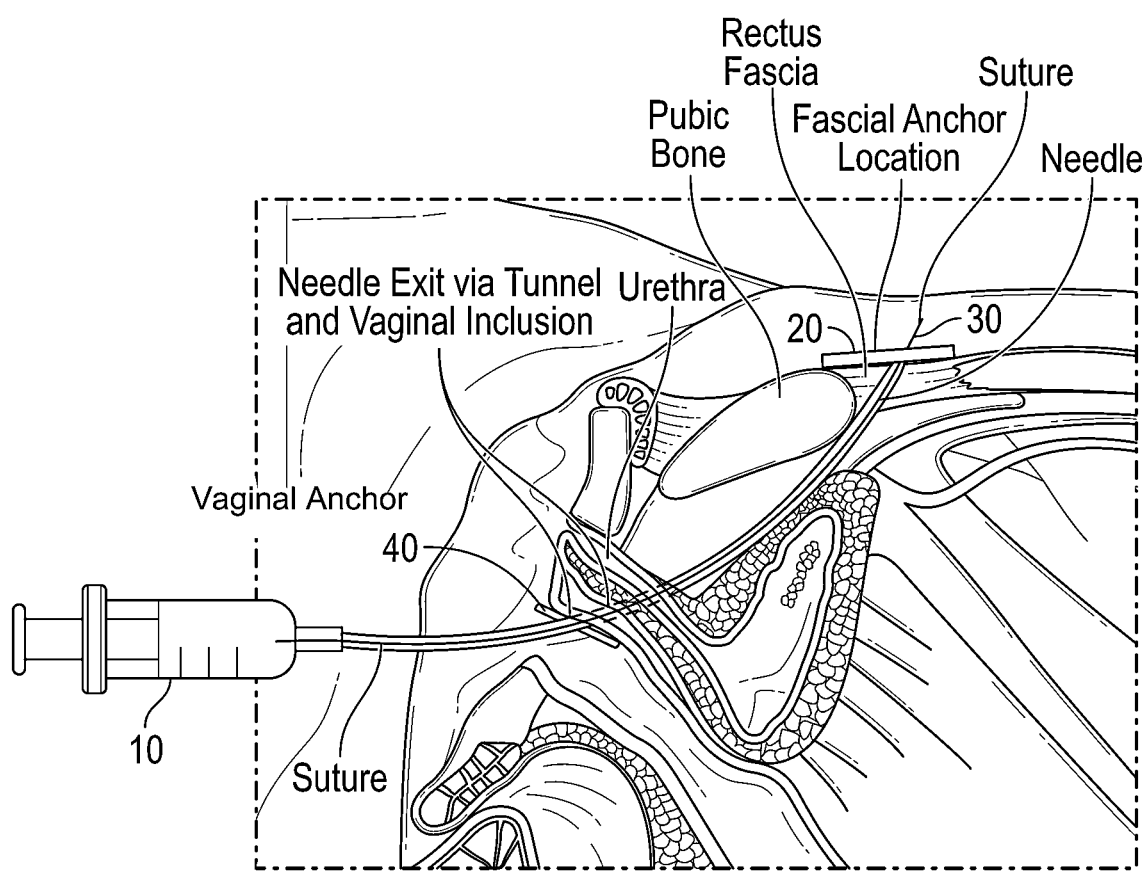
FIG. 3A illustrates an example of a needle path laying approximately in the sagittal plane for delivering and deploying an anchor in accordance with the present disclosure.
Figure 3B:
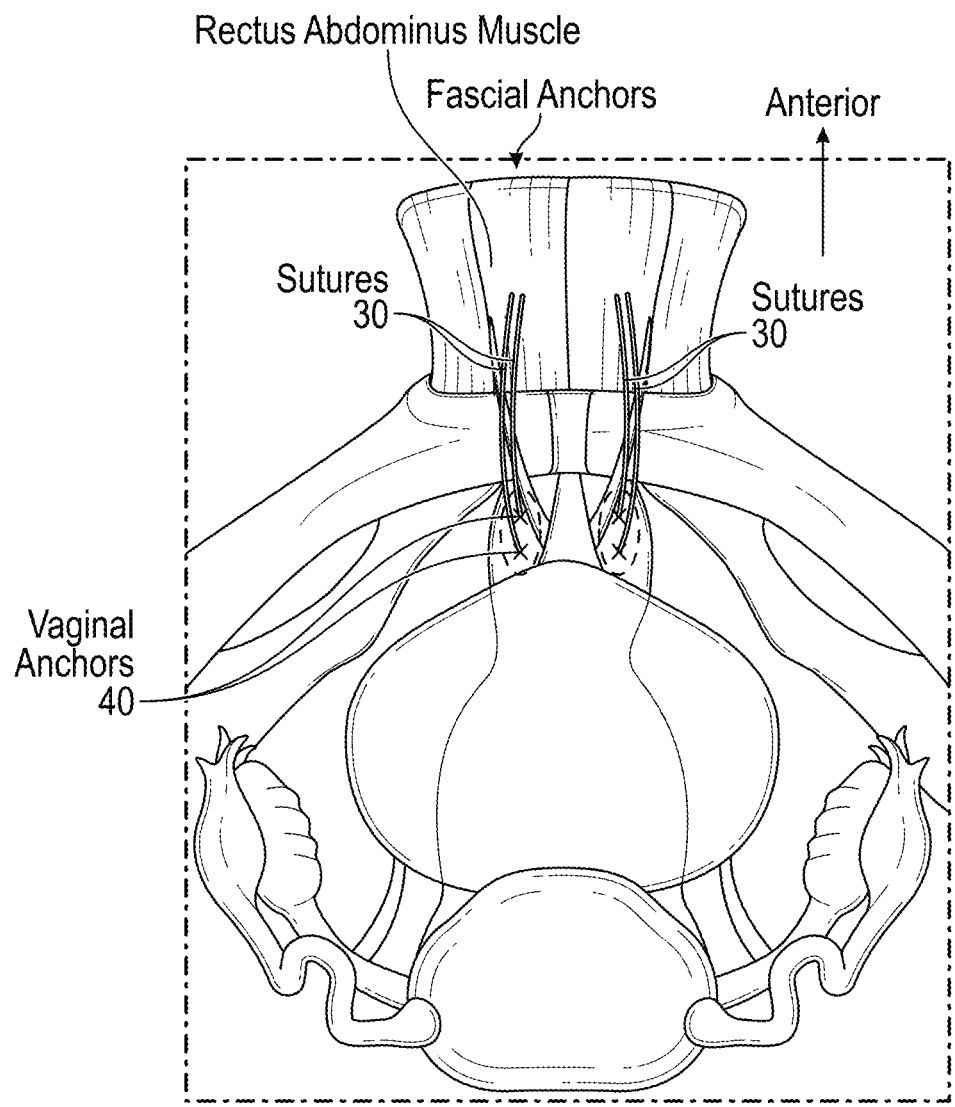
FIG. 3B presents an example of placement of anchors and sutures in accordance with the present disclosure along an anatomical viewing angle that is oblique to the transverse anatomic plane.

In some implementations, and with reference to FIGS. 3A and 3B, an illustrative procedure begins by first placing a urinary catheter, such as a conventional Foley-type catheter, into the urethra and into the bladder and inflated at its distal end to hold it in place (not shown). The bladder is drained by way of the urinary catheter. Alternatively, a catheter as described in U.S. Patent Application Ser. No. 63/012,056, filed Apr. 17, 2020, which is incorporated by reference herein in its entirety, can be used instead. The catheter of the '056 application (or a different catheter) can be further modified (or specially configured) to include a further light source, such as a LED light, at a location corresponding to the mid-urethra of the patient, which is located about two centimeters from the bladder neck, since the female urethra is about four centimeters in length. A second light source such as a LED can be included in the catheter at the point of the mid-urethra, or a light conductive medium can be used to conduct light from the light source in the urinary catheter located just past the neck of the bladder downwardly to a location about two centimeters from the bladder neck. For example, if the catheter includes an opaque covering over a light transmissive layer (e.g., an inner tube), the opaque covering can be stripped away or otherwise not be present at the location of the mid-urethra to permit light to shine through the catheter that can be viewed inside of the patient, but outside of the urethra, for example, with an endoscope (not shown) in the peritoneal/pelvic cavity, to inform the surgeon where to place the needle laterally with respect to the mid-urethra to deliver the required sutures. Illumination of the mid-urethra can guide the surgeon both as to the correct level of placement as well as prevent the surgeon from placing the needles too close to the urethra. After placement of the urinary catheter, a local anesthetic (e.g., 0.5% Marcaine or similar) is applied to numb the local anatomy.

The delivery system 10 that includes a (e.g., 1-2 mm) hollow applicator needle, defining a lumen along at least a part of its length can then be inserted through the vagina, lateral to the urethra on each side for placement of each of four sutures, preferably under direct visualization of an endoscope. It will be appreciated that fewer or more sutures 30 can be used. Reference numbers 30, 130 and 242a are used herein to refer to sutures, tethers, suture loops, and the like. For each suture 30 placement, the needle, as illustrated in FIG. 3A, is directed behind the pubic bone and then through the rectus fascia. The rectus fascia is thick and strong and permits the surgeon to feel a discernable "pop" when the needle passes through it. Once the needle is through the rectus fascia, the surgeon then advances the fascial anchor 20 forward through the lumen of the needle and permits the anchor 20 to expand, and/or carries out one or more further manipulation steps to expand the fascial anchor. The fascial anchor 20 can have an X-shape, a star shape, a barbed section, disc shape, or the like, for example, once deployed, although further implementations are described below. The fascial anchor 20, thread or suture 30, and vaginal anchor 40 are each preferably, but not necessarily, made from resorbable material. After each of the four fascial anchors 20 are placed, the hollow delivery needle is withdrawn, leaving the suture or thread 30 extending into the vaginal canal. After all four sutures are delivered, there are two punctures on either side of the urethra through the anterior vaginal wall, wherein one is located approximately parallel to the bladder neck and the other is located approximately parallel to the mid-urethra.

Next, each thread or suture pair 30 on either side of the urethra is threaded through the vaginal anchor 40, which can also be made of PDS or other bioresorbable material. The sutures 30 can then be placed under tension and the vaginal anchor 40 is gently pushed upwards. The sutures 30 can then be secured in place to hold the vaginal anchor 40 in place, and tied together or otherwise crimped, trapped, or secured in place.

Preferably, the vaginal anchor 40 is oblong and smooth walled in order to minimize patient discomfort and to minimize the profile of the anchor. If resorbable PDS anchors and sutures are used, the anchors and sutures can be expected to dissolve in about six months. During that time, the elevated bladder neck will scar in place and can be expected to maintain the effects of the procedure for a long term basis. FIG. 3B further illustrates relative placement of the vaginal anchors 40 (behind the anterior vaginal wall, and the placement of the four sutures through the rectus abdominus. Instead of the rectus abdominus, the sutures 30 and/or anchors 40 can alternatively be directed through the obturator internus muscle, or in one or more or a combination of locations.

After the procedure, however, it may be desired to adjust the fit of the vaginal anchor. For example, the suspension can prove to be too tight. This can manifest itself, for example, in the patient having a hard time emptying their bladder. In this instance, the installation can be modified by un-securing the sutures 30 (e.g., by untying a knot or unlocking a lock that holds them in place), the vaginal anchor 40 can be loosened slightly, and the sutures 30 can be re-secured. On the other hand, the suspension can be too loose, for example, if the patient still has urinary leakage. In this instance, the sutures 30 can be unfastened, the vaginal anchor can be raised to reduce the distance between the fascial anchor 20 and the vaginal anchor 40, and the sutures 30 can then be refastened. The patient will typically realize that either condition has occurred within a couple of days, long before the repair has had time to scar in place.

While the sutures can be unknotted and loosened and retied, in further implementations, the free ends of the suture can be held in place in the anchor by a clamping force or a friction lock for example, that can have an engaged and disengaged position. The vaginal anchor can be unlocked so that the suture may slide through it, and then locked in order to prevent the suture from moving. The suture can traverse a serpentine path when traversing through the lock, for example. The anchor can be engaged or disengaged with the suture, as appropriate, by way of depressing an actuator or a friction lock incorporated into the suture path, or by toggling a mechanical switch that, in a first position, locks the suture in place, and in a second position, lets the suture slide through the vaginal anchor. In the case of a friction lock, the suture path can include a wedge shaped lock that can include teeth or undulations, for example, that slides into a keyed slot that when fully inserted jams the suture in place, and when partially retracted, permits the suture to move freely or under a detectable amount of physical resistance. If a barbed suture is used, the barbs can be directed in a manner to prevent the vaginal anchor from being loosened, and an unlocking mechanism can include a tubular member or other device that is advanced over the barbs to collapse them to permit the vaginal anchor to be adjusted.

Figure 4:
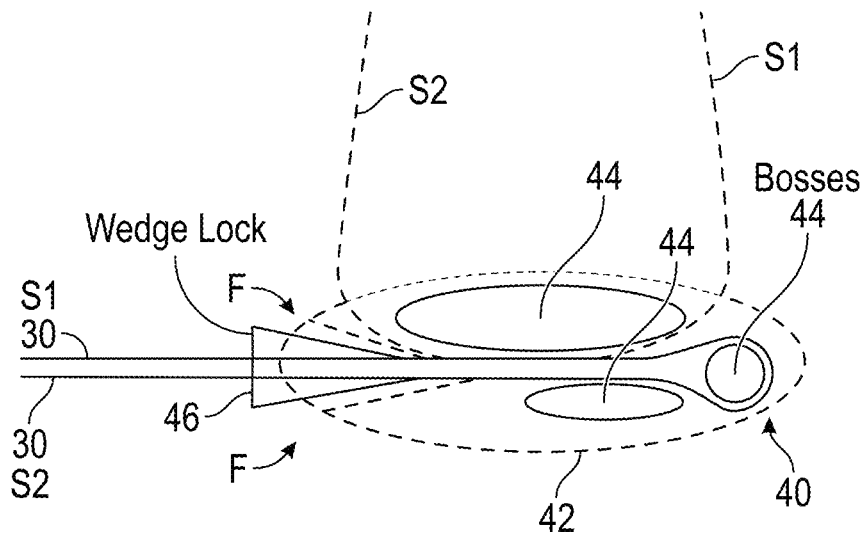
FIG. 4 presents a schematic of one example of a vaginal anchor in accordance with the present disclosure.

FIG. 4 presents a schematic of one example of a vaginal anchor 40 in accordance with the present disclosure. The anchor 40 can be bounded by an atraumatic low profile lozenge-like body 42 and includes first and second suture entrances for receiving sutures 30 (S1 and S2) on an upper side of the anchor, and a suture exit port that can be directed toward the vaginal entrance that can include a mechanical lock 46, such as a wedge lock that is received by an interference fit inside of the lock body. The wedge body of the lock 46 can be disengaged, for example, by a suitably configured hand tool (not shown). The suture S1, which is located further inside the vagina than suture S2 is directed around a smooth boss 44 and through an opening in the wedge shaped lock body and out of the vaginal anchor. Suture S2 enters through the top of the lock, is directed along a direction away from an entrance to the vagina where it is looped around a further boss permitting it to turn 180 degrees, pass by a third boss over which the suture slides, and out through the lock body. It will be appreciated that the lock mechanism of the anchor if so provided, can be configured in a multitude of ways. But, it is preferred that the sutures can enter into the top of the vaginal anchor and exit through the bottom, or an end of the anchor. In another embodiment, one or both of the sutures can exit through a lateral side of the vaginal anchor, as desired. It will be appreciated that the vaginal anchor can be configured to receive one tether, or three or more tethers, as desired.

Figure 5:
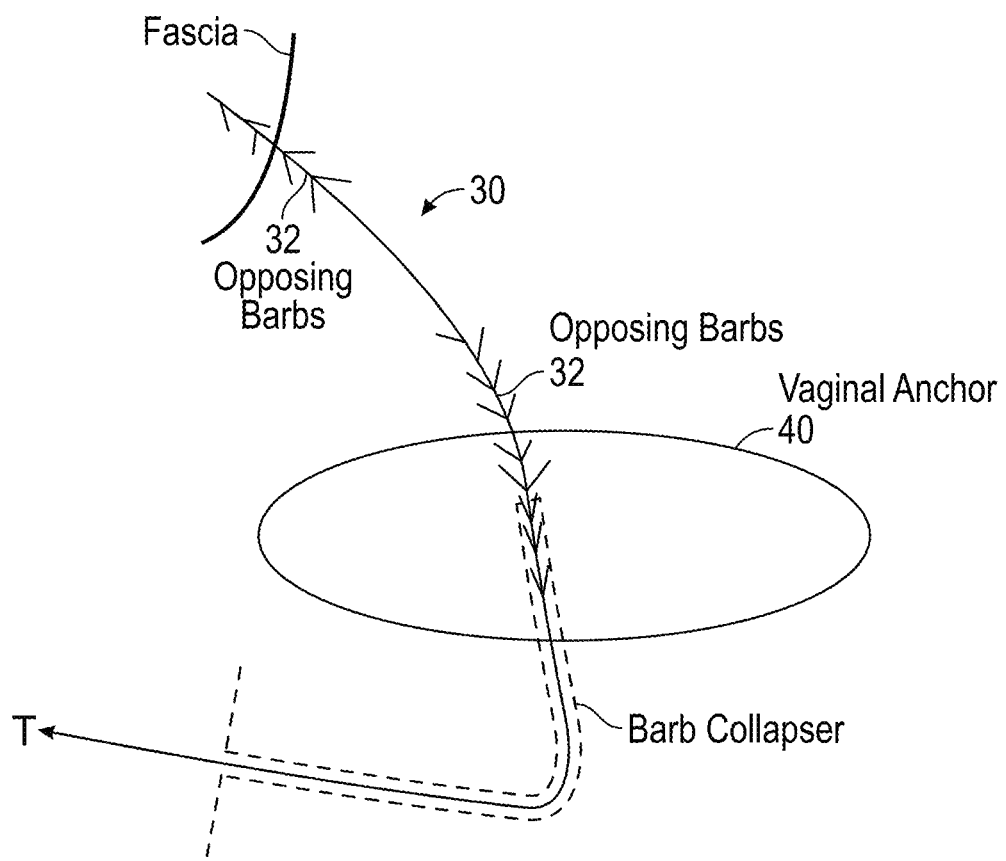
FIG. 5 presents a schematic of a further example of a vaginal anchor in accordance with the present disclosure.

FIG. 5 presents a schematic depicting aspects of a further embodiment of a vaginal anchor in accordance with the present disclosure. As depicted, a suture 30 with barbs 32 facing in opposing directions is provided that is directed through the fascia as described above wherein the barbs prevent the suture from backing out. A second portion of the suture has opposing faced barbs to pass through the vaginal anchor. The barbs can be collapsed by advancing a tubular tool or hollow needle over the suture to permit the anchor to be loosened. Tightening the anchor can be accomplished by simply advancing the anchor over the barbs of the barbed suture.

Figure 6A:
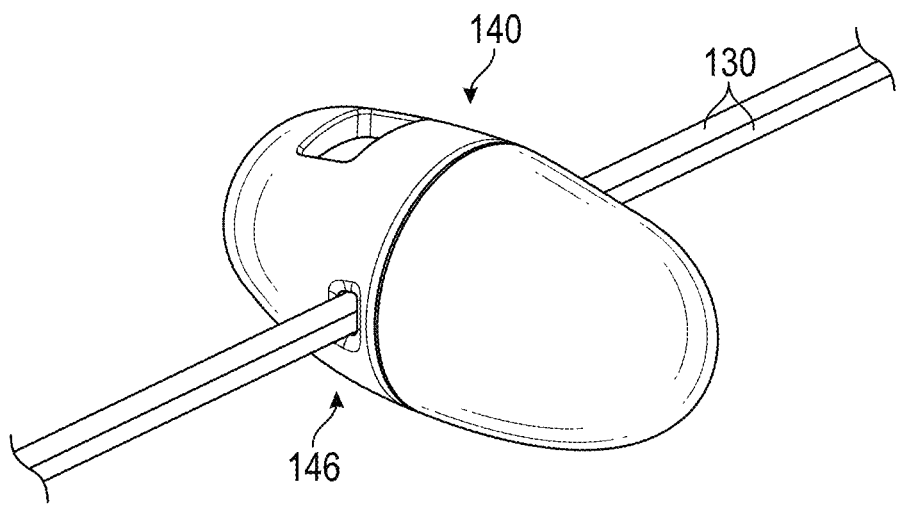
FIGS. 6A-6B are isometric views of a further implementation of a vaginal anchor in accordance with the present disclosure in a fully locked position into a pair of sutures.
Figure 6B:
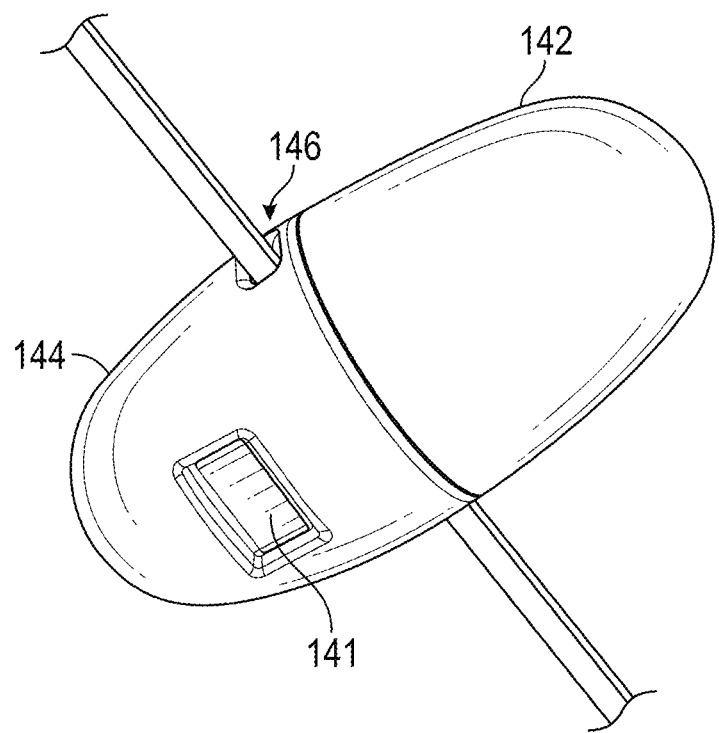
Figure 7A:
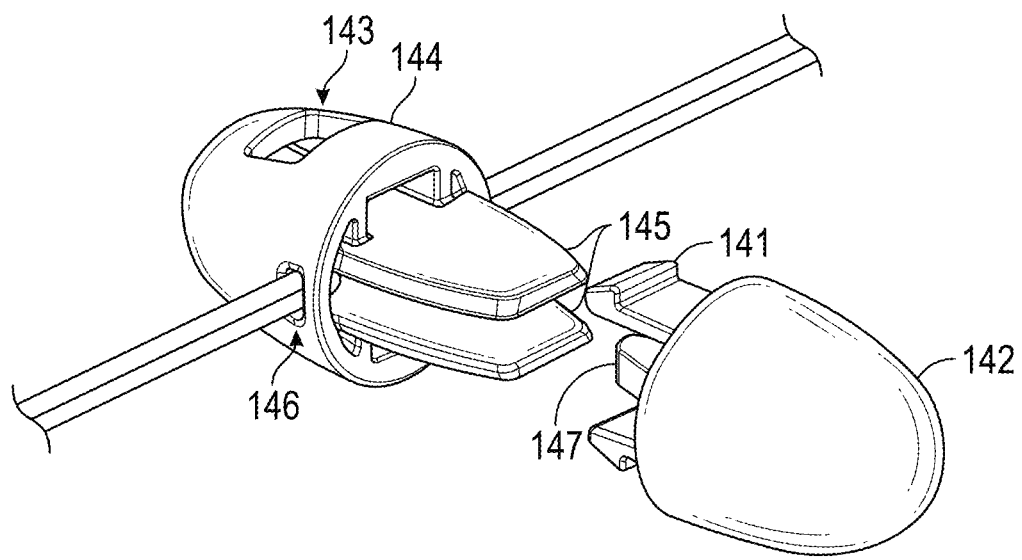
FIGS. 7A-7B are isometric views of the vaginal anchor of FIGS. 6A-6B in an exploded condition illustrating certain internal components of the vaginal anchor.
Figure 7B:
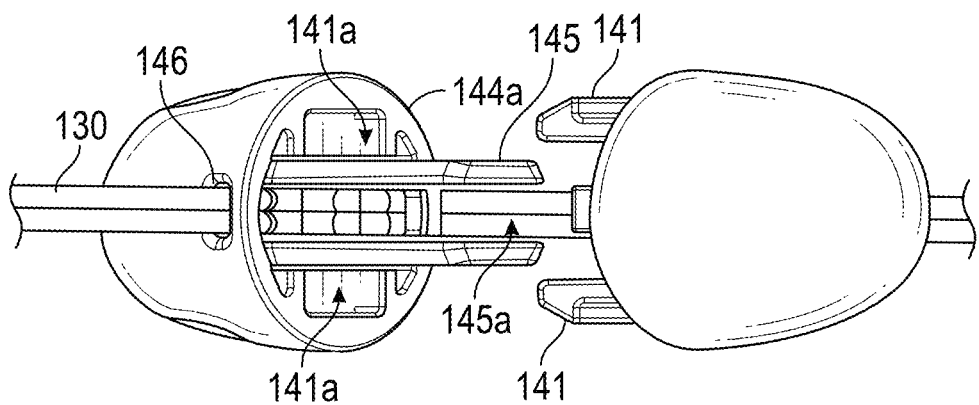

FIGS. 6A-6B are isometric views of a further implementation of a vaginal anchor in accordance with the present disclosure in a fully locked position into a pair of sutures. FIGS. 7A-7B are isometric views of the vaginal anchor of FIGS. 6A-6B in an exploded condition illustrating certain internal components of the vaginal anchor.

As depicted, anchor 140 is composed of two interlocking portions 142, 144 that cooperate to form a generally continuous outer surface that has an elliptical projection from the side and a generally circular projection in an end view. It will be appreciated that anchor 140 can be modified to be any general shape and operate in a manner similar to that described herein. Interlocking portion 144 of anchor defines a pair of openings 146 through a sidewall thereof that receive one or more sutures or tethers 130 therethrough to be locked in place. FIG. 6A depict the anchor 140 in a condition wherein the two interlocking portions 142, 144 are fully locked in position, wherein a respective barb 141 on each lateral side of interlocking portion 142 is received into a corresponding pair of barb receiving openings 143 defined through the sidewall of interlocking component 144. While it is not needed to provide an opening 143 that receives the barb 141 of the housing component 142, providing openings 143 can be useful as it permits a tool (not shown) such as forceps or the like to press radially inwardly on the barbs 141 if a physician or surgeon desires to unlock the anchor 140 from the suture 130.

With reference to FIGS. 7A and 7B, as can be seen, housing component 144 includes a pair of spaced apart generally parallel plates 145 that define a cavity 145a therebetween through which sutures 130 pass, as well as through openings 146 in the sidewall 144a of component 144. The plates 145 are generally tongue-shaped, and each said plate 145 is received by a corresponding cavity 142a (FIG. 12B) of housing component 142. Each plate 145 extends outwardly from the peripheral wall 144a of the housing component 144. Housing component 142 defines two outwardly extending arms having barbs 141 thereon that slide into corresponding cavities, or tracks 141a within housing component 144. Housing component 142 further defines an outward projection 147 that is slidably received within cavity 145a of housing component 144 that urges against sutures 130 to hold them in place within housing component 144.

Figure 8A:
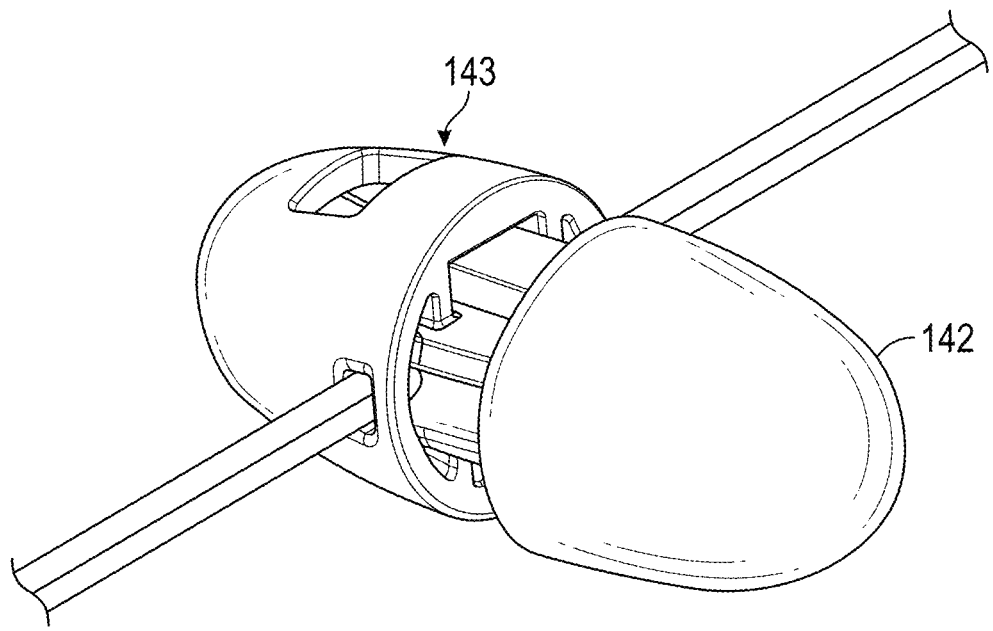
FIG. 8A is an isometric view of the vaginal anchor of FIGS. 6A-6B in a partially locked position.
Figure 8B:
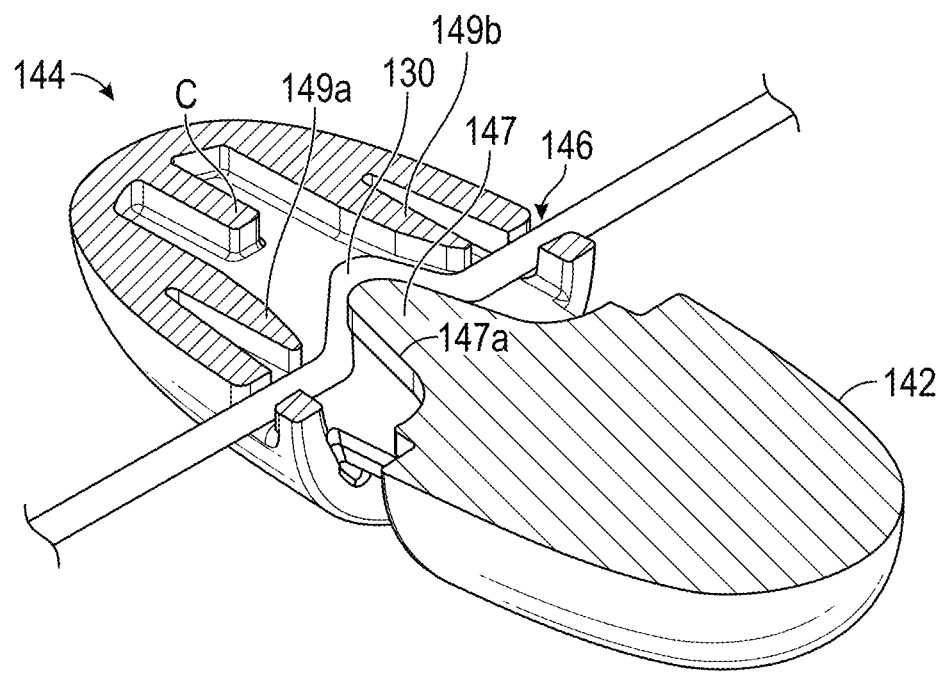
FIG. 8B is a section isometric view of the vaginal anchor in the partially locked position of FIG. 8A.
Figure 10A:
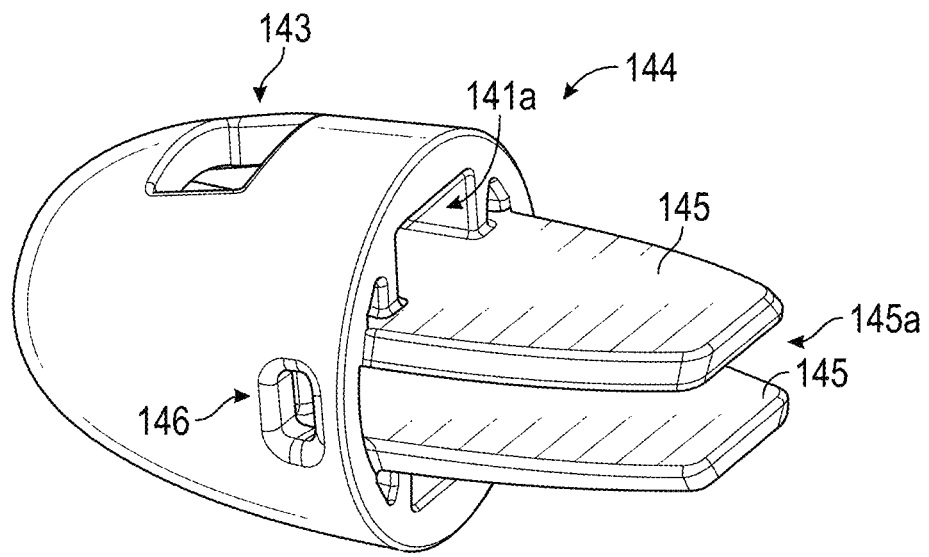
FIG. 10A is an isometric view of a portion of the vaginal anchor of FIGS. 6A-6B.
Figure 10B:
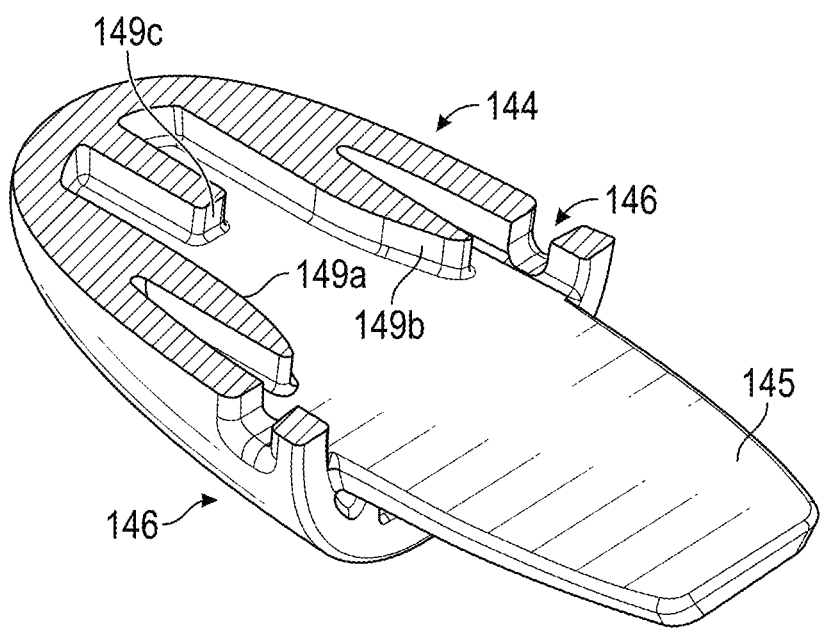
FIG. 10B is a sectional view of the portion of the vaginal anchor as set forth in FIG. 10A.

FIG. 8A is an isometric view of the vaginal anchor of FIGS. 6A-6B in a partially locked position. FIG. 8B is a section isometric view of the vaginal anchor in the partially locked position of FIG. 8A. When in this configuration, anchor 140 will permit the anchor 140 to be slid along suture(s) 130 with some resistance as the physician or surgeon is adjusting tension on the tethers 130 during the procedure. Once the surgeon or physician believes that they have the anchor 140 correctly positioned, the anchor can be snapped into place. As can be seen in FIG. 8B, the interior of anchor component 144 defines a plurality of bearing surfaces 149a, b, c against which the suture 130 is pressed when anchor 140 is in a fully locked position by a corresponding curved end face 147a of projection 147. FIGS. 10A-10B are further views of component 144 (isometric and isometric cutaway, respectively) showing the relative placement of internal components.

Figure 9A:
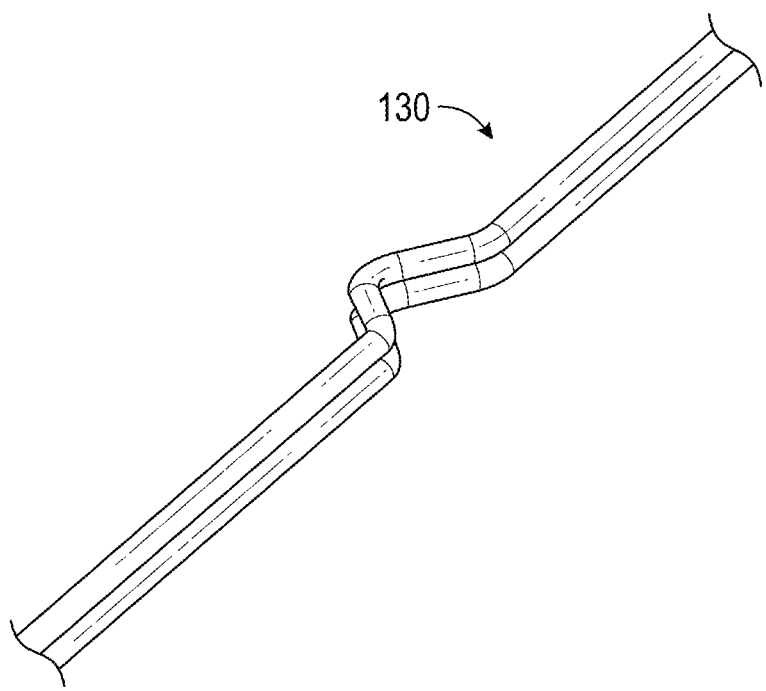
FIG. 9A is an isometric view of a pair of sutures in an arrangement wherein the vaginal anchor is in a partially locked position as illustrated in FIG. 8B.
Figure 9B:
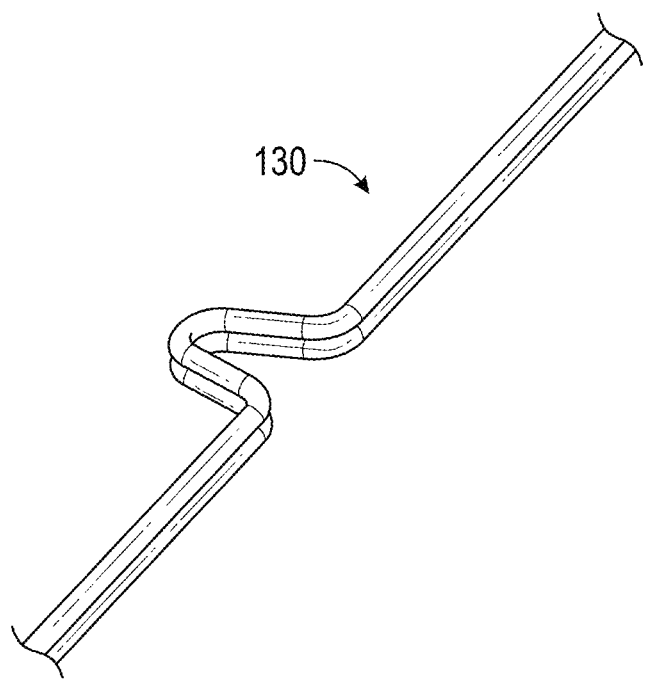
FIG. 9B is an isometric view of a pair of sutures in an arrangement wherein the vaginal anchor is in a fully locked position as illustrated in FIGS. 6A-6B.

FIG. 9A is an isometric view of a pair of sutures in an arrangement wherein the vaginal anchor 140 is in a partially locked position as illustrated in FIG. 8B. FIG. 9B is an isometric view of a pair of sutures in an arrangement wherein the vaginal anchor is in a fully locked position as illustrated in FIGS. 6A-6B. As can be seen, in the fully locked position as illustrated in FIG. 9B, the sutures 130 traverse a considerably more tortuous path than in the partially locked condition of FIG. 9A.

Figure 11A:
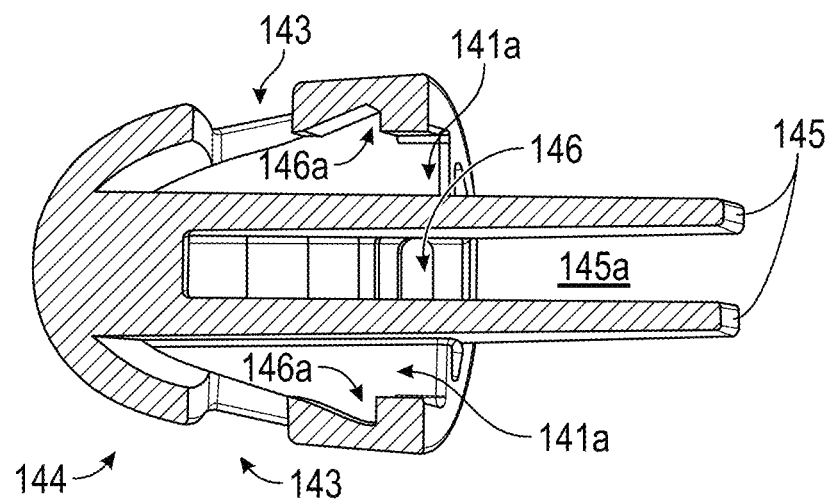
FIGS. 11A-11B are a cross sectional view of the vaginal anchor FIGS. 6A-6B showing internal components of both portions of the anchor.
Figure 11B:
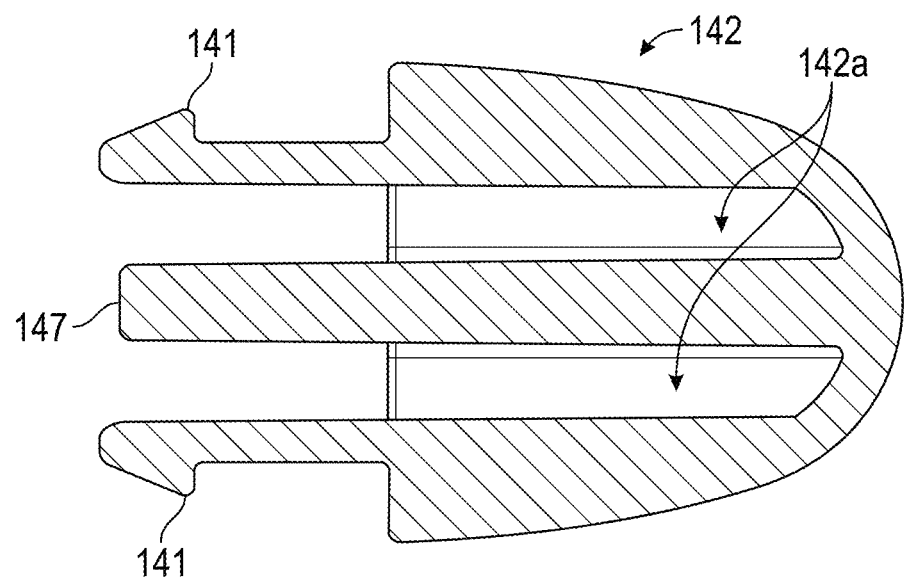

FIGS. 11A-11B are a cross sectional view of the vaginal anchor FIGS. 6A-6B showing internal components of both portions of the anchor. As illustrated, this cross section is orthogonal compared to the cross section of FIG. 8B, for example. As to component 142, clearly illustrated in cross section are cavities 142a that receive projections 145 and cavity 145a that receives projection 147. Barbs 141 on deflectable cantilevered arms that extend axially away from the outer periphery of component 142 are also depicted, as well as cavities 141a that receive arms with barbs 141 within component 144. Further illustrated are catches or cavities 146a that receive the barbs 141 when the anchor is in the intermediate or partially locked orientation of FIGS. 8A-8B.

Figure 12A:
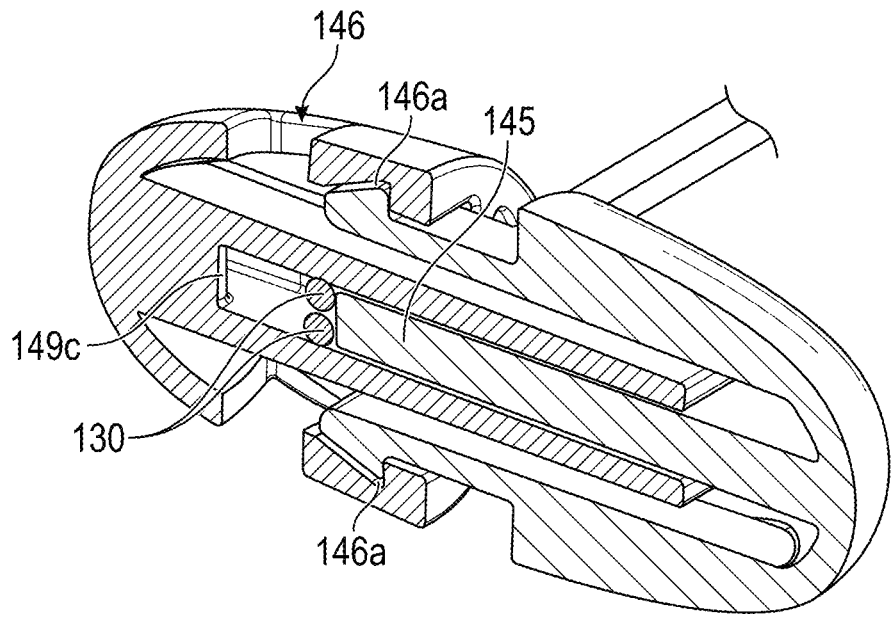
FIG. 12A is an isometric cross-sectional view of the vaginal anchor FIGS. 6A-6B showing the anchor in a partially locked position.
Figure 12B:
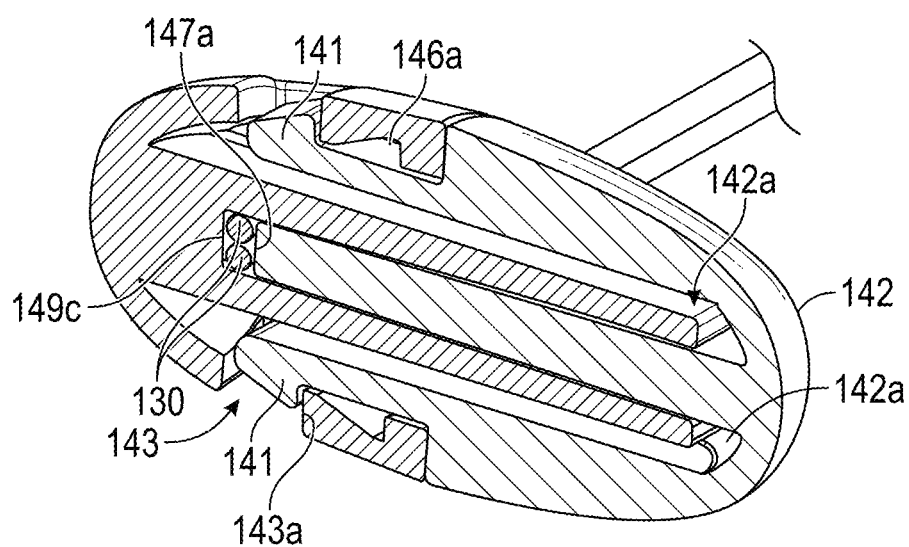
FIG. 12B is an isometric cross-sectional view of the vaginal anchor FIGS. 6A-6B showing the anchor in a fully locked position.

FIG. 12A is an isometric cross-sectional view of the vaginal anchor of FIGS. 6A-6B showing the anchor 140 in a partially locked position. As can be seen, in this position, the barbs 141 are received by cavities 146a of component 144. The sutures 130 are shown in cross section. FIG. 12B is an isometric cross-sectional view of the vaginal anchor FIGS. 6A-6B showing the anchor in a fully locked position. In this orientation the sutures are fully trapped and held in place between surfaces 149c and 147a, and barbs 141 are held in place against surfaces 143a that partially define opening 143.

Figure 13A:
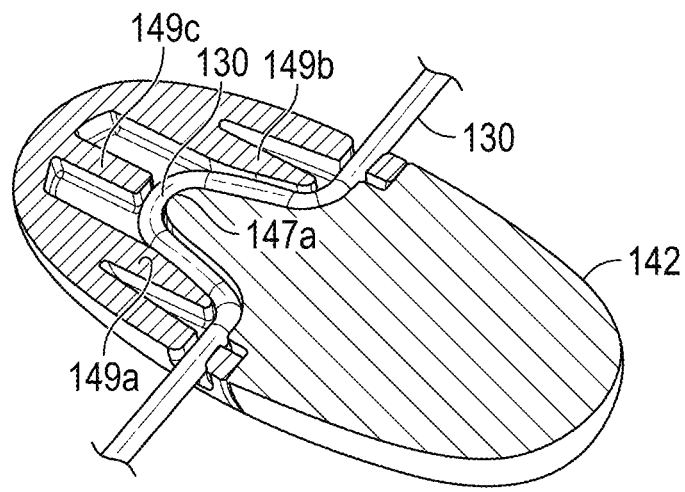
FIG. 13A is an isometric cross-sectional view of the vaginal anchor FIGS. 6A-6B showing internal components of the anchor holding the suture in place in a fully locked position.
Figure 13B:
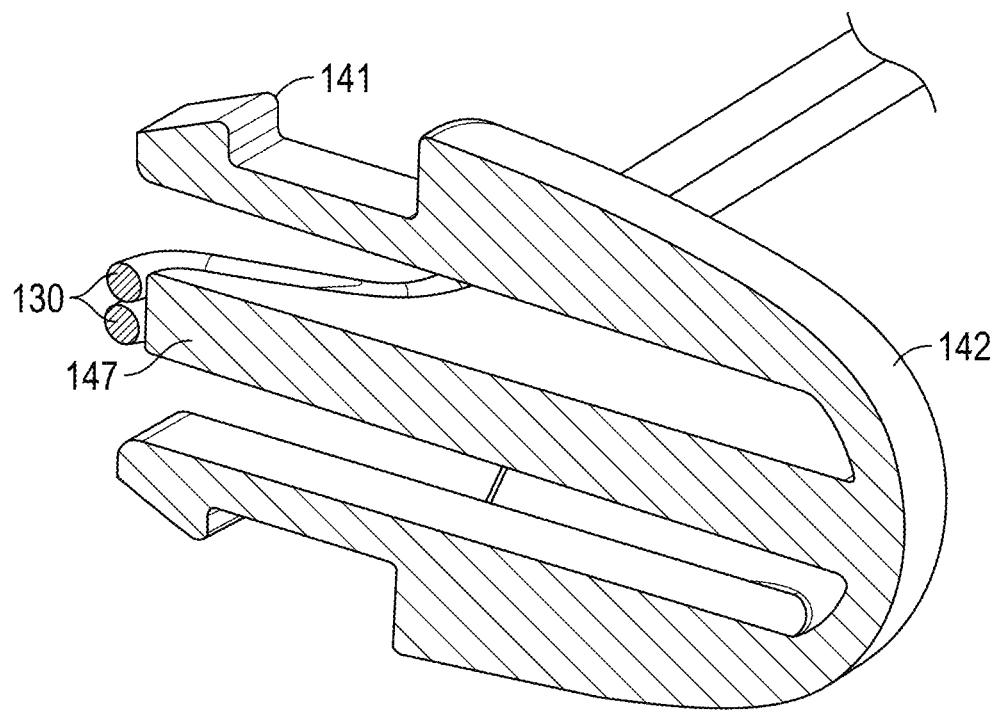
FIG. 13B is a further isometric cross-sectional view of the vaginal anchor FIGS. 6A-6B showing internal components of the anchor holding the suture in place in a fully locked position.

FIG. 13A is an isometric cross-sectional view of the vaginal anchor FIGS. 6A-6B showing internal components of the anchor holding the suture in place in a fully locked position. As can also be seen in this view, the suture 130 is compressed by the curved surface 147a against surface 149c as well as the surfaces of components 149a and 149b when the anchor 140 is in the fully locked configuration. FIG. 13B is a further isometric cross-sectional view of component 142 of the vaginal anchor FIGS. 6A-6B rotated 90 degrees about a central longitudinal axis of the anchor 140, showing internal components of the anchor holding the suture in place in a fully locked position, particularly illustrating barbs 141 and protrusion 147 and its relative location with respect to sutures 130.

Figure 14:
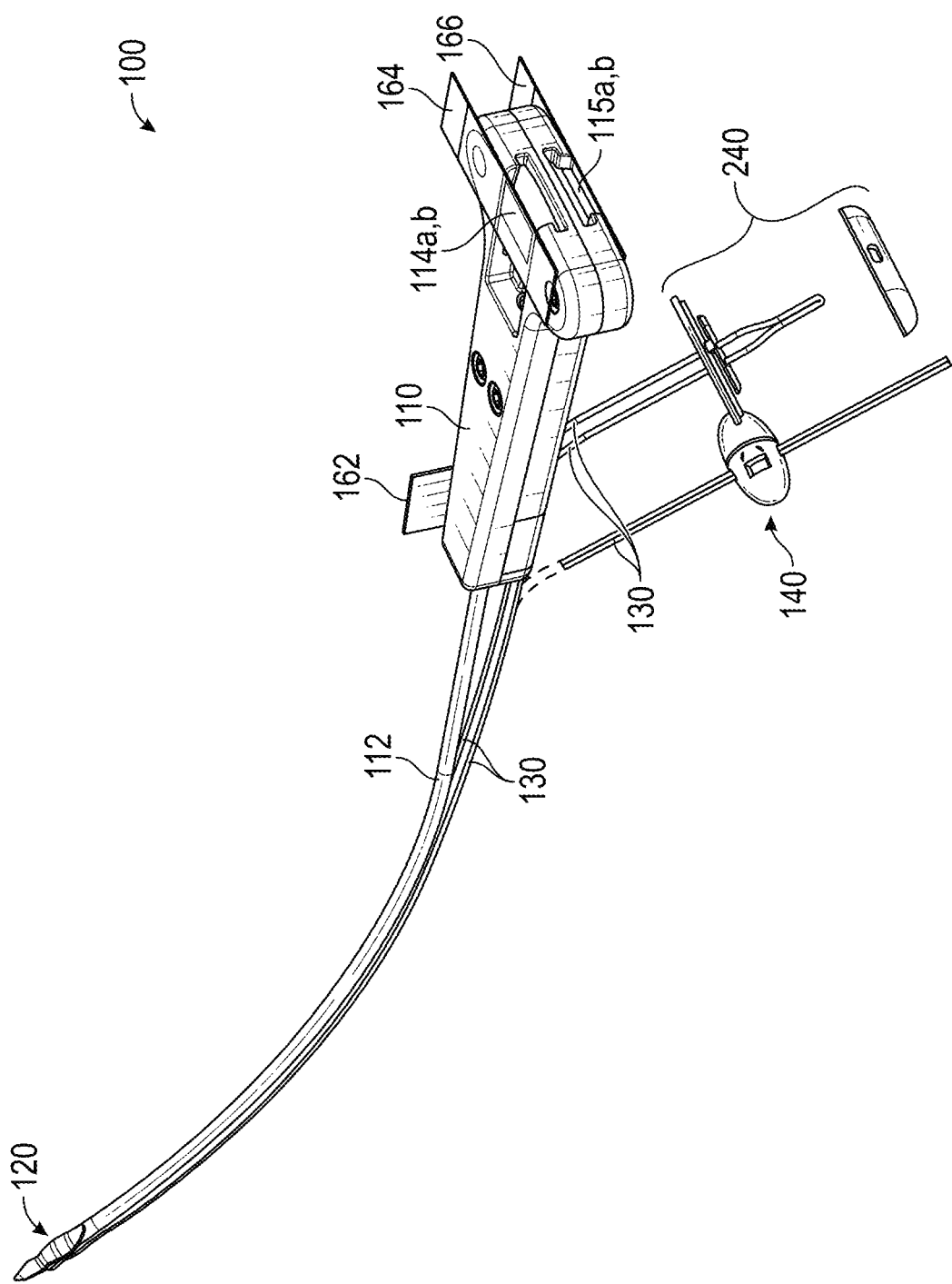
FIG. 14 is an upper isometric view of a representative embodiment of a delivery system in accordance with the present disclosure.

FIG. 14 is an upper isometric view of a representative embodiment of a delivery system 100 also referred to herein as a system 100 or device 100 in accordance with the present disclosure. It will be appreciated that the depictions and description of system 100 and aspects thereof is merely illustrative and not intended to be limiting in any way.

Generally, system 100 includes a handle or housing 110 that includes actuator handles to actuate pull rods or push rods wires that travel down a hollow shaft 112 to a distal portion that includes a fascia anchor 120. Further illustrated are vaginal anchor 140 in relative position, as well as a further implementation of a vaginal anchor 240 described in further detail below with reference to FIGS. 40-44B.

Suture material 130, which can be in the form of a single length of suture, for example, can extend from a proximal end of the device 100, held in place by a cleat, clamp or removable tape 162, for example, and extend along an external surface of hollow shaft 112, through a body component of a fascia anchor 20 located at a distal end of the device 100, back along the shaft 112, and proximally toward the handle 110 wherein both free ends of the suture are held in place by a retainer or tape 162, for example. The device 100 is used to advance the anchor and shaft 112 through the top of the vaginal wall, through the patient's tissue, and through fascia tissue as described above until the distal anchor portion 120 has passed through the fascia. At this point, the suture 130 has been pulled along through the passage defined through the tissue by the device 100, and the anchor can be deposited beyond and/or in the fascia of the patient, holding the anchor in place. The shaft 112 and pushrods therein are removed, leaving behind the anchor, and the sutures, which trail into the vagina. The vaginal anchor (e.g., 140, 240) is then threaded over the free ends of the sutures, tensioned, and locked in place as generally described above.

Figure 15:
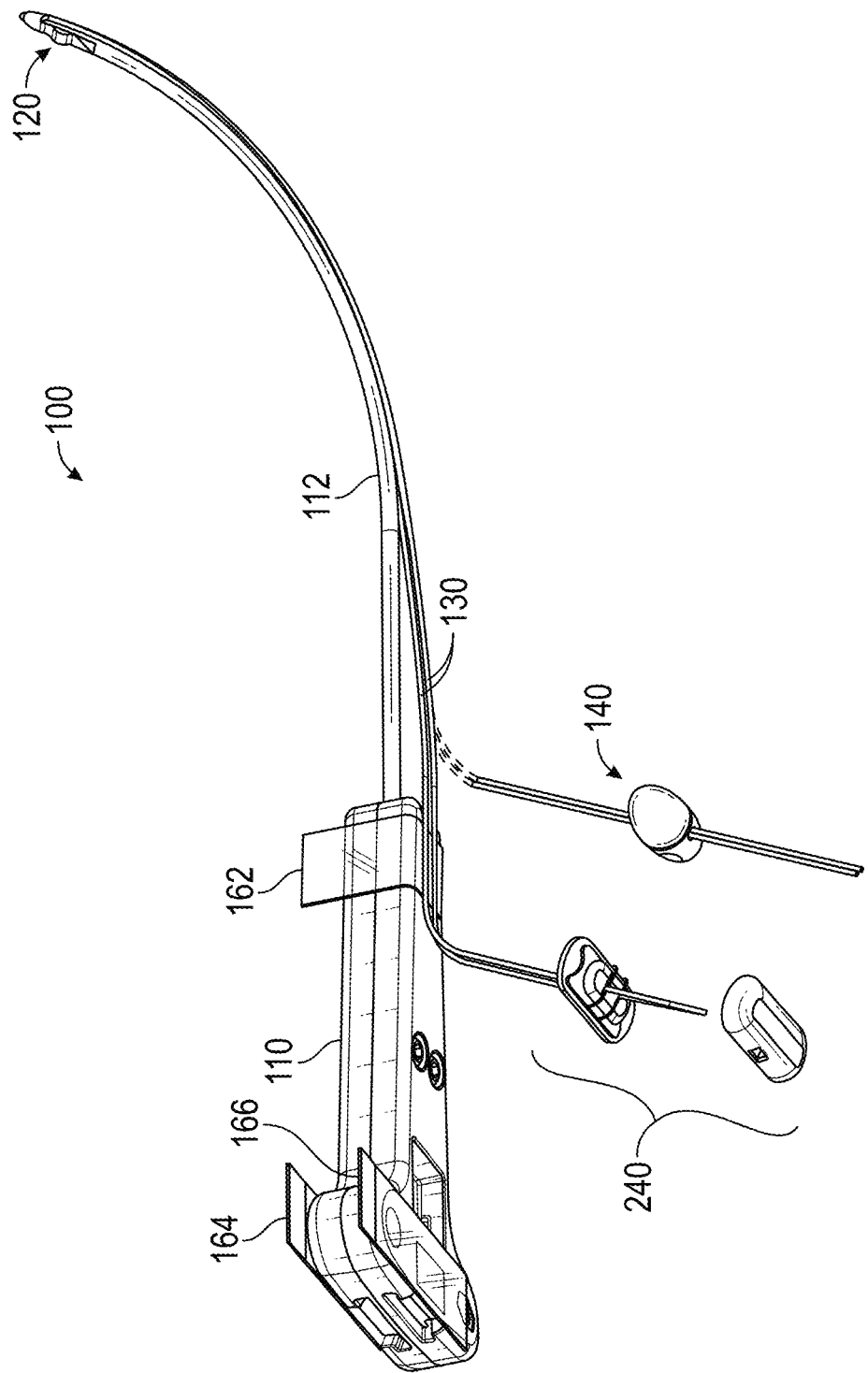
FIG. 15 is a lower isometric view of a representative embodiment of a delivery system in accordance with the present disclosure illustrated in FIG. 14.

More particularly, as depicted, the system 100 incudes a housing or handle 110 having three removable adhesive panels (e.g., adhesive tape), wherein a first tape 162 holds the free ends of the suture 130 against the underside of the housing, a second tape 164 holds an actuator handle 114a,b that is coupled to a pushrod (described in further detail below) in place with respect to the housing, and a third tape 166 holds an actuator 115a,b coupled to a retractable wire or rod in place against the housing 110. Tubular member 112 extends proximally into the handle within a passage 110c defined within the handle or housing 110. Tubular member extends distally and terminates in fascia anchor assembly 120. FIG. 15 is a lower isometric view of the embodiment of FIG. 14.

Figure 16:
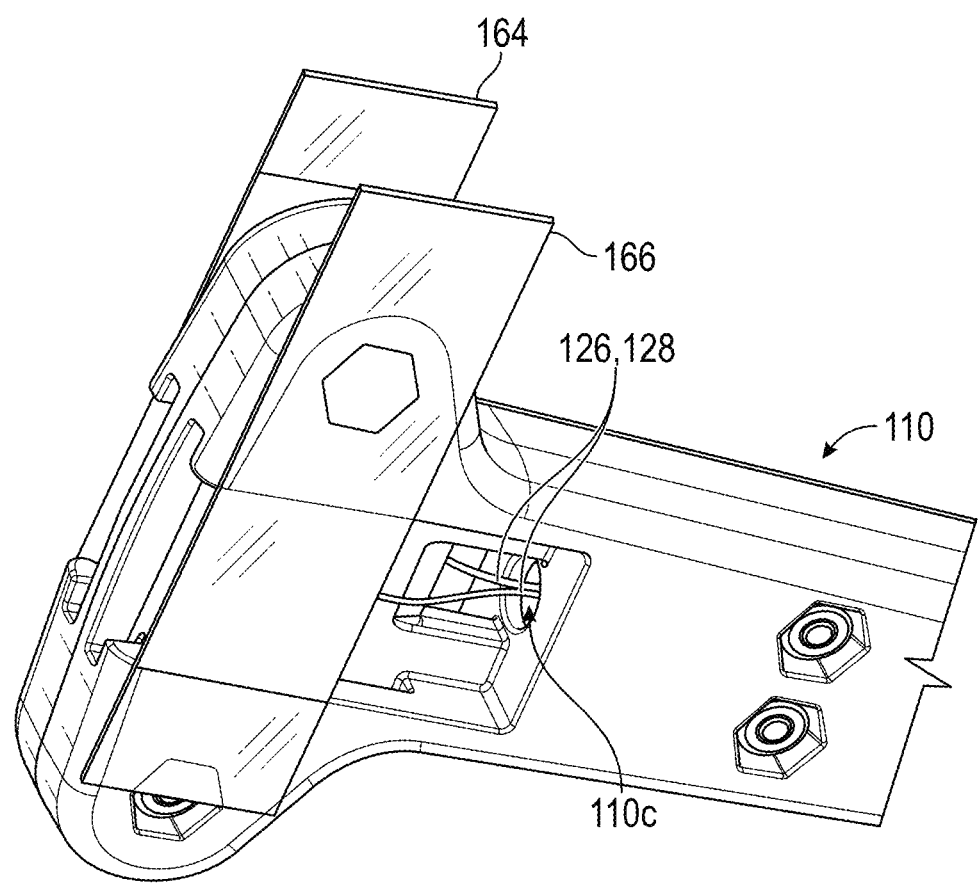
FIG. 16 is an enlarged view of a proximal portion of the delivery system of FIG. 14.

FIG. 16 is an enlarged view of a proximal portion of the delivery system of FIG. 14 from underneath the housing 110. Wires or rods 126, 128 are visible extending from the actuators 114, 115 into a passageway 110c defined through the housing that further extend into tubular member 112 toward the distal end of the system 100.

Figure 17:
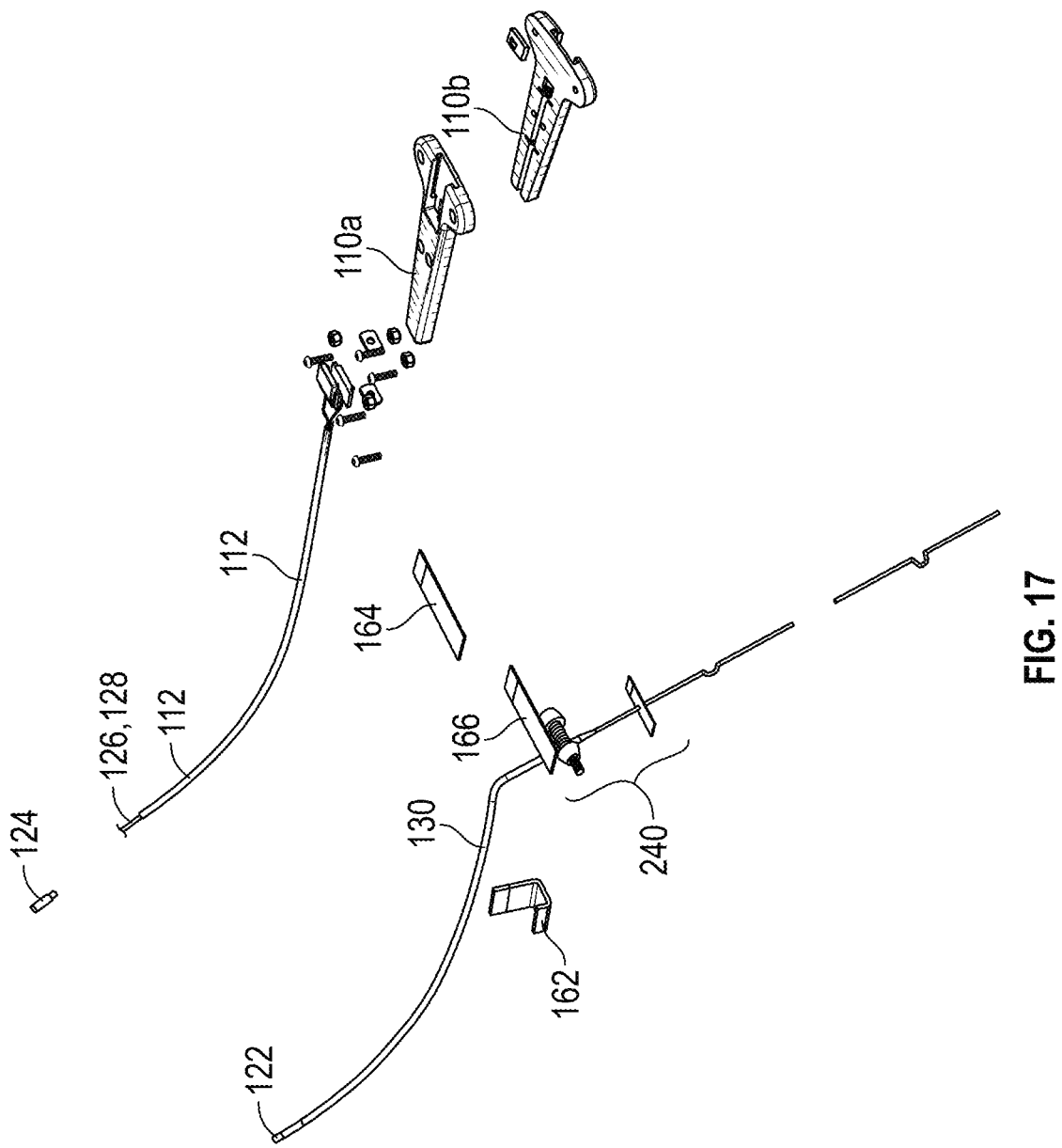
FIG. 17 is an exploded view of the delivery system of FIG. 14.

FIG. 17 is an exploded view of the delivery system of FIG. 14. Certain hardware components (screws and the like) are illustrated in various of the views based on the exploded view of FIG. 17. However, it will be appreciated that the threaded fasteners used to hold the handle or housing 110 together are only one of many possible arrangements in accordance with the disclosure. As illustrated, the handle is composed in this example of two housing components 110a, 110b that couple to tubular member 112 that terminates in two wires 126, 128 that couple to proximal portion 124 of anchor assembly 120. Also illustrated are the suture loop 130 that is routed through distal portion 122 of the anchor assembly 120, as well as tapes 162, 164, 166 and anchor 240, described in further detail below.

Figure 18:
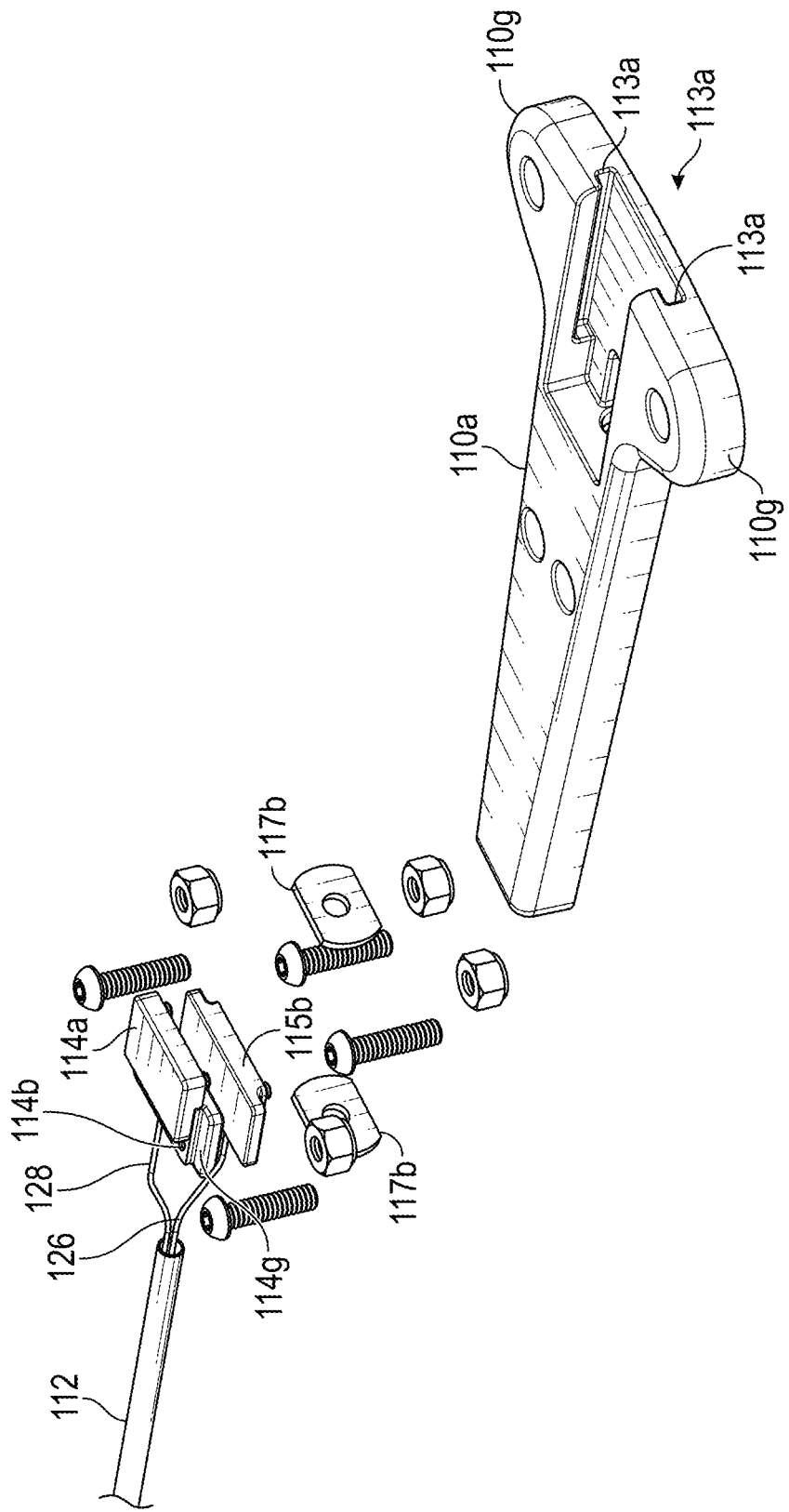
FIG. 18 is a close-up view of the exploded view of FIG. 17 illustrating aspects of a handle portion of the delivery system of FIG. 14.

FIG. 18 is a close-up view of the exploded view of FIG. 17 illustrating aspects of a handle portion of the delivery system of FIG. 14. As illustrated in the present example, an actuator block 114 is presented that can be unitary or formed from two portions 114a, 114b to entrap a proximal end of a wire 128. A portion 115b of lower actuator block 115 is also illustrated that couples to a proximal end of wire 126. As can be seen, each of wires 126, 128 traverse through a lumen defined along the entire length of the tubular member 112. Retainer plates 117b are received in grooves defined in the housing components, discussed below. Plates can also be attached (e.g., by adhesive and the like) to tubular member 112.

Figure 19A:
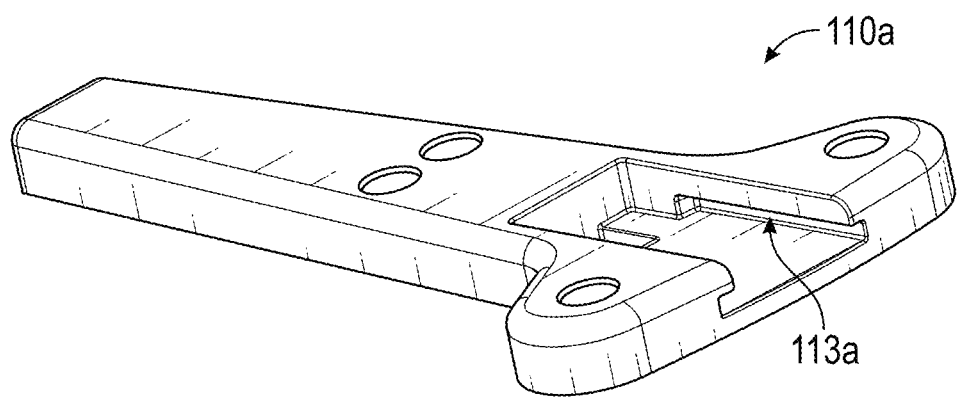
FIGS. 19A-19C present upper isometric, proximal isometric, and lower isometric views of a first portion of a housing of the delivery system of FIG. 14.
Figure 19B:
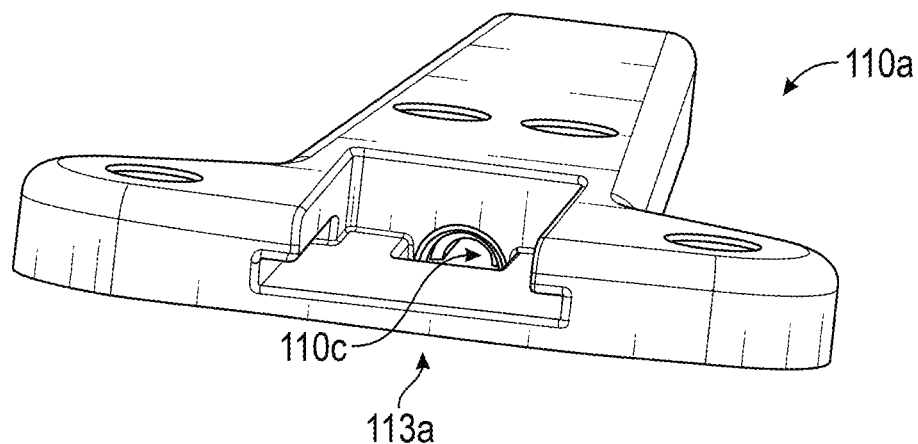
Figure 19C:
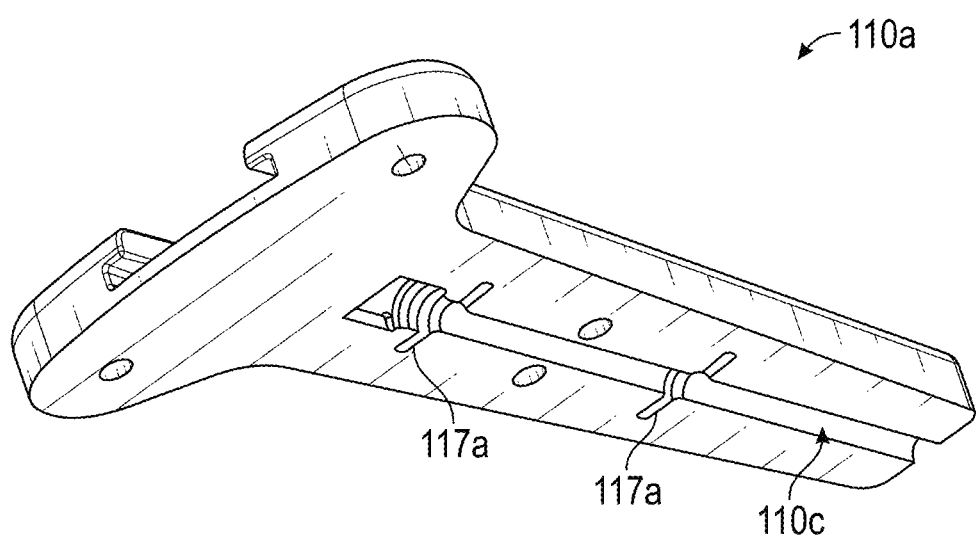

With continuing reference to FIGS. 18, an upper view of upper portion 110a of housing 110 is depicted. As illustrated, the housing can be elongate and include proximal grip portions 110g, if desired. Housing component 110a further defines a channel, or groove 113a therein that is characterized by a main channel that begins at a proximal end of the device and extends distally. Channel further includes one or more undercuts or the like 113u that form guide tracks along the main channel to receive a corresponding tab 114j of the upper actuator block 114. FIGS. 19A-19C present upper isometric, proximal isometric, and lower isometric views of a first portion 110a of a housing 110 of the delivery system 100 of FIG. 14. As is visible, housing components 110a defines a split lengthwise portion of an elongate axial passage 110c along its length to receive a proximal region of tubular member 112 secured in plates 117b that are in turn received by slots 117a defined in an underside of housing component 110a. FIG. 19B illustrates that the passage 110c terminates at its proximal end at the distal end of channel 113a.

Figure 20A:
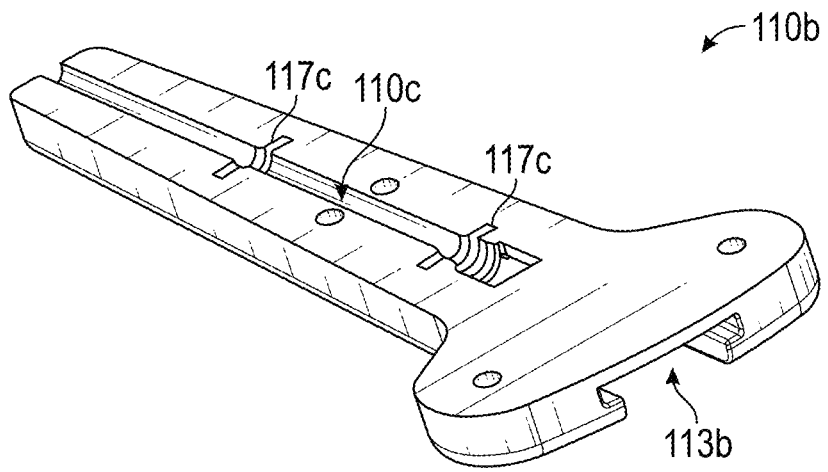
FIGS. 20A-20B present upper isometric, and lower isometric views of a second portion of a housing of the delivery system of FIG. 14.
Figure 20B:
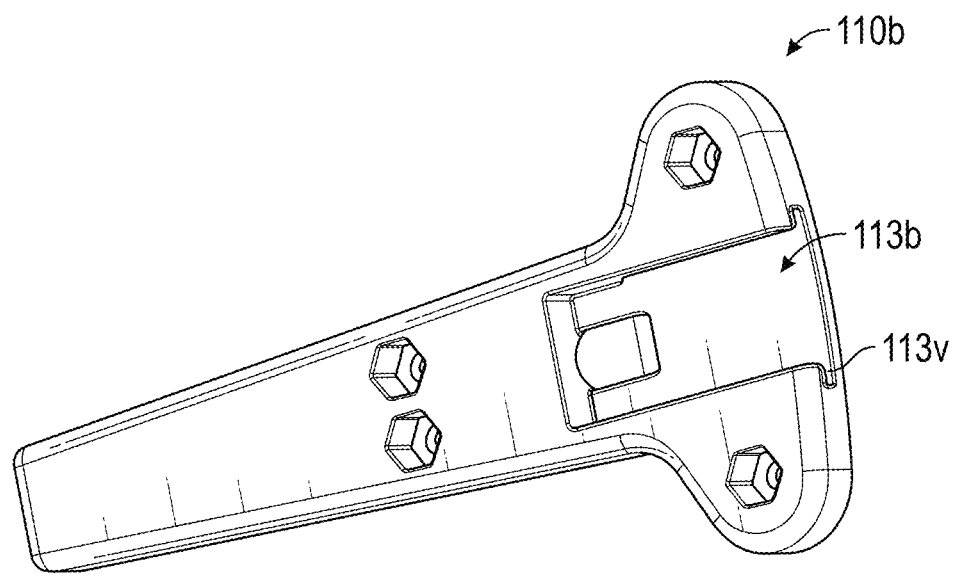

FIGS. 20A-20B present upper isometric, and lower isometric views of a second portion 110b of a housing of the delivery system of FIG. 14. Housing component 110b can essentially be a mirror image of component 110a, defining a corresponding second portion of channel 110a that receives tubular portion 112 and slots 117c that receive plates 117b, which in turn hold and orient tubular member 112. A similar channel 113b with side guide rails, or undercuts 113v are defined in the lower surface of the housing component 110b.

Figure 21A:
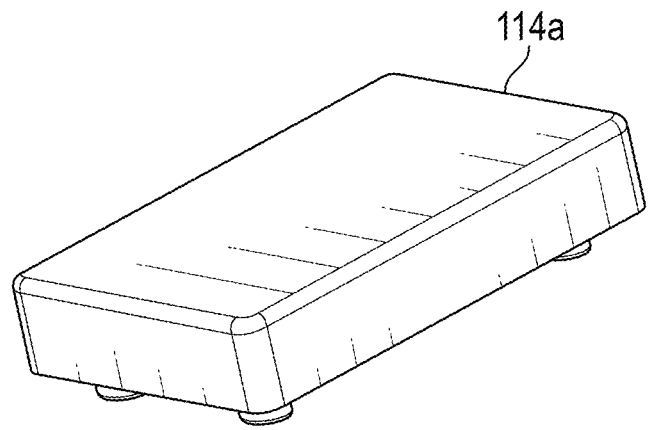
FIGS. 21A-21B are upper isometric and lower isometric views of a portion of a retainer block of the delivery system of FIG. 14.
Figure 21B:
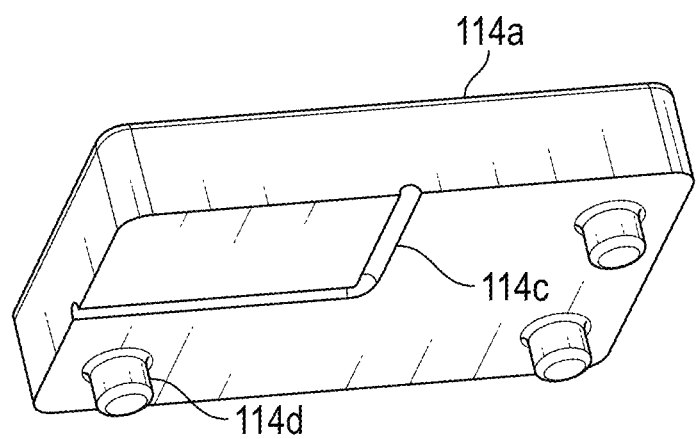
Figure 22:
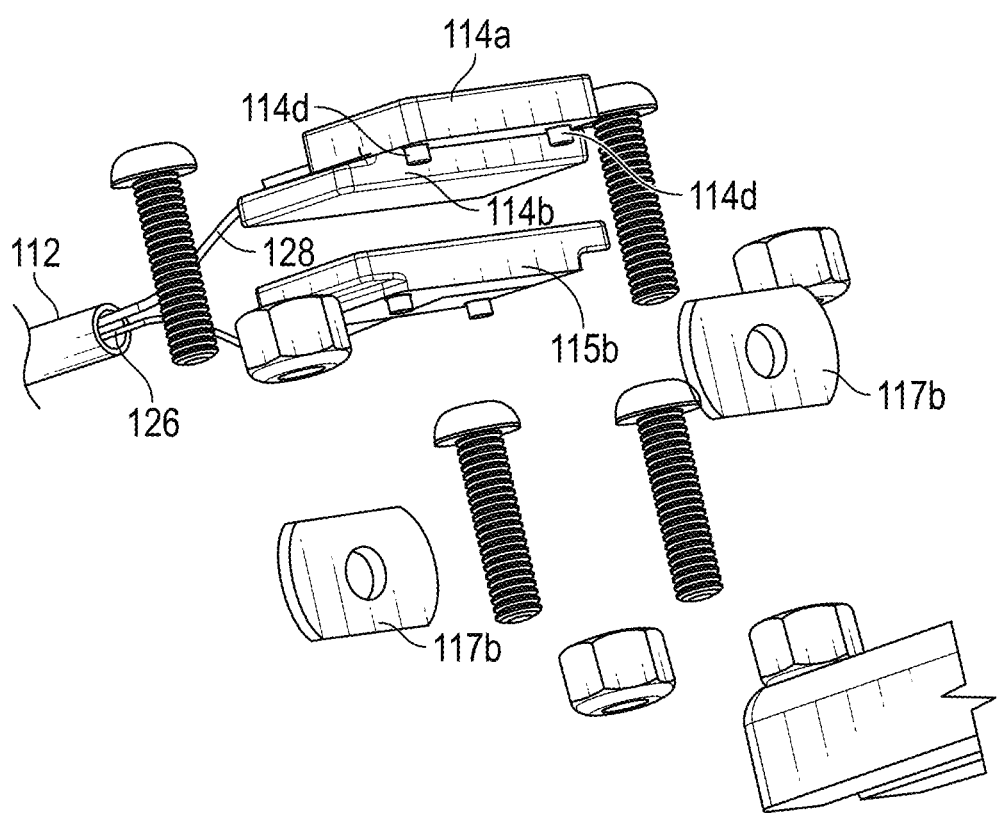
FIGS. 22-24 are a partial isometric exploded views of a portion of the delivery system of FIG. 14 illustrating aspects of retainer blocks of the system and guide and alignment plates of the delivery system.
Figure 23:
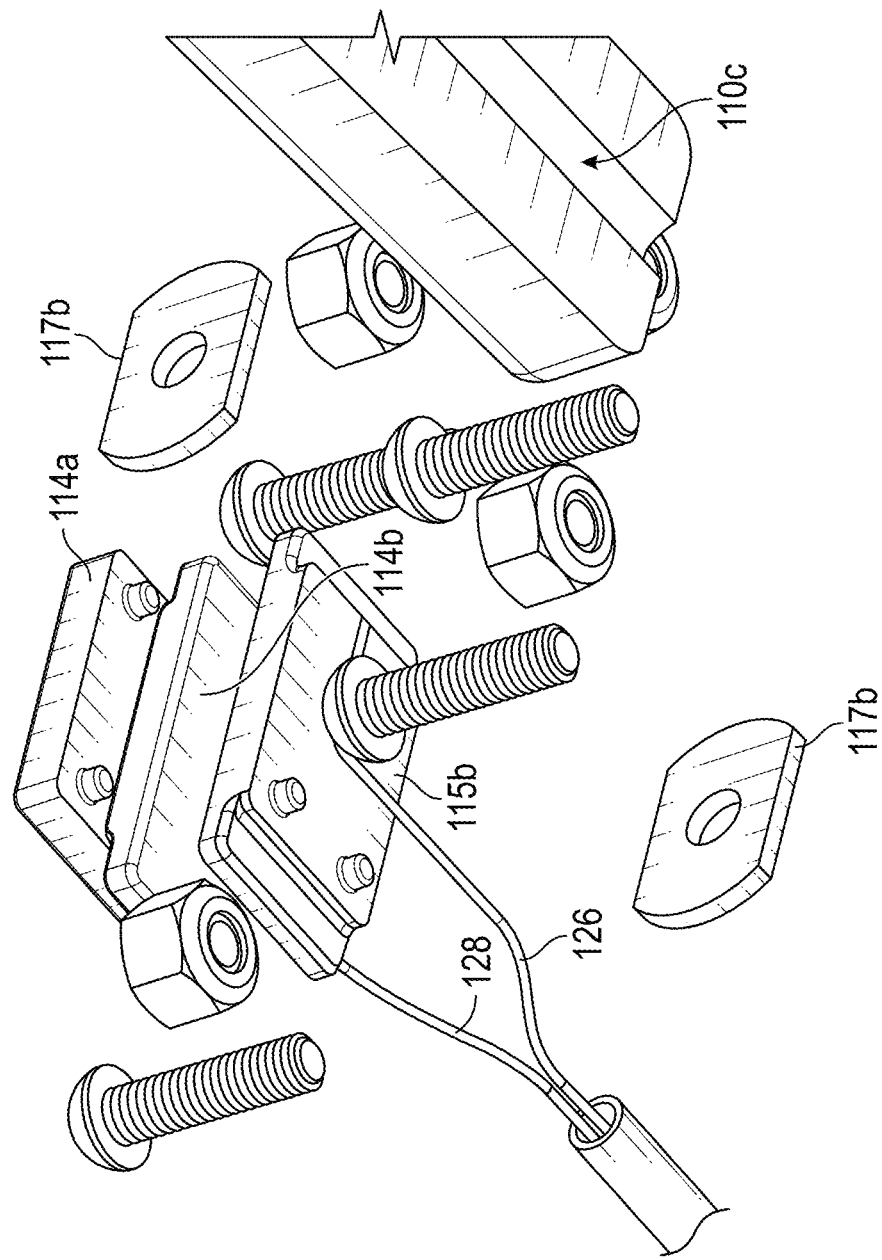
Figure 24:
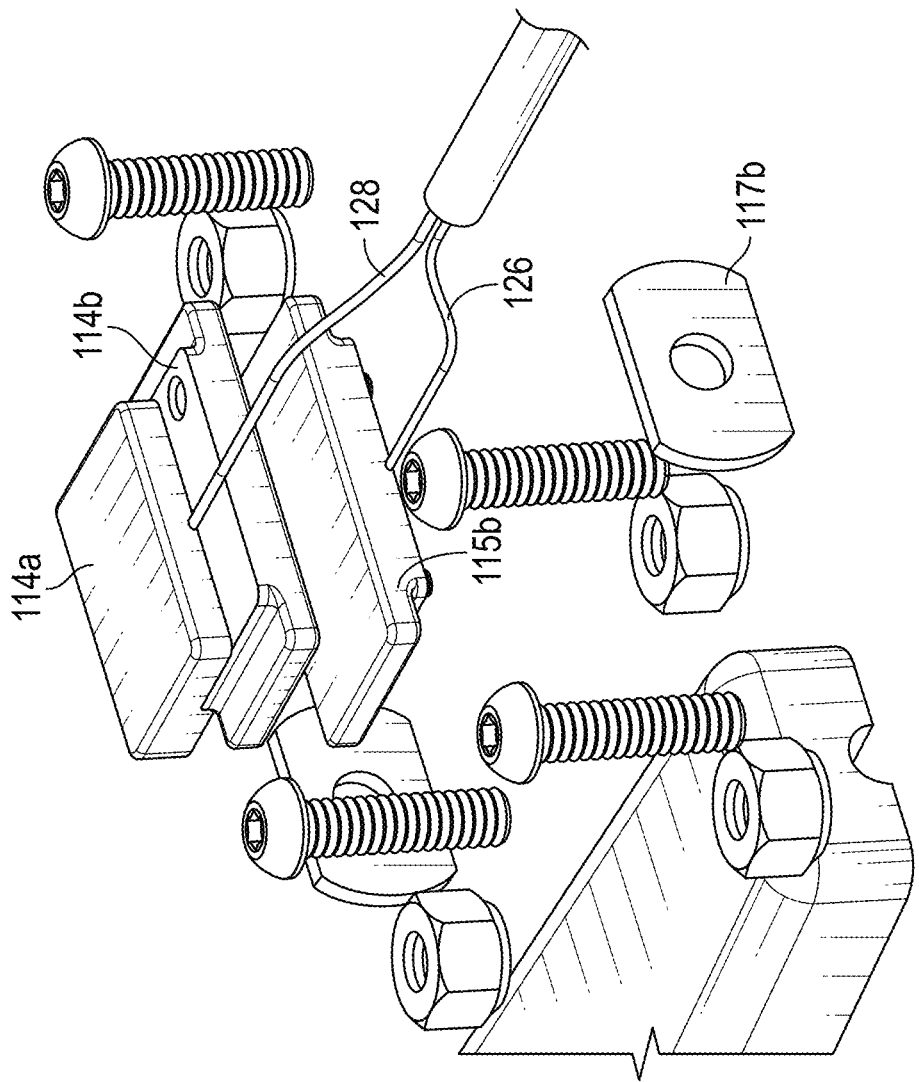
Figure 25A:
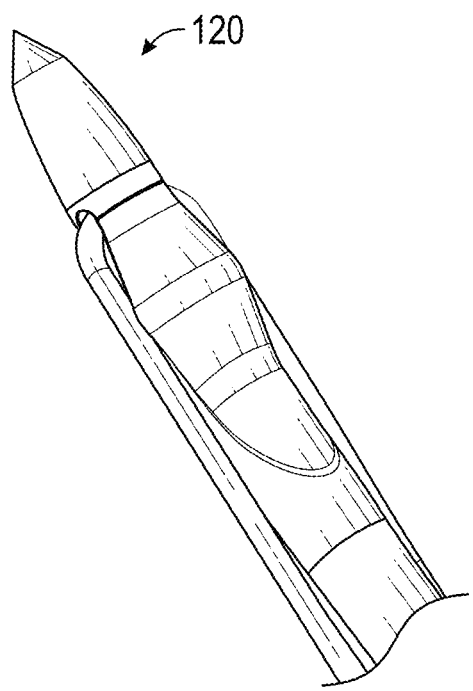
FIGS. 25A-26B are enlarged isometric views of a distal portion of the system of FIG. 14 illustrating aspects of a fascial anchor portion of the system.
Figure 25B:
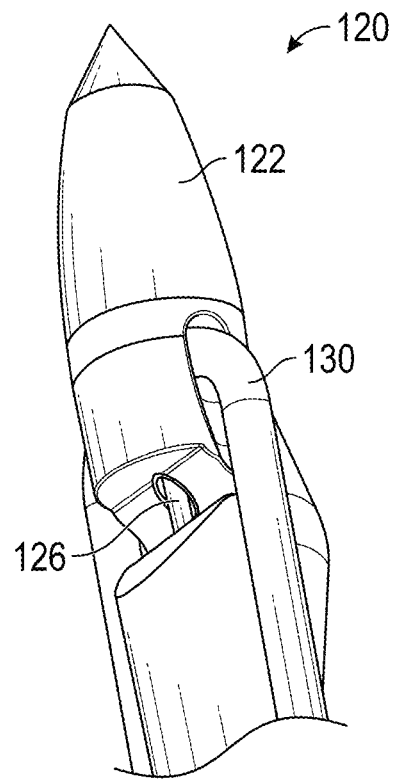

FIGS. 21A-21B are upper isometric and lower isometric views of a portion 114a of a retainer block 114 of the delivery system of FIG. 14. Block defines a groove 114c in an underside thereof that bends along its path to hold a proximal end of wire 128 in place. One or more attachment bosses 114d (or pegs glued into recesses) can be provided that are received by corresponding sockets of block 114b. FIGS. 22-24 are a partial isometric exploded views of a portion of the delivery system of FIG. 14 illustrating aspects of retainer blocks of the system and guide and alignment plates of the delivery system. FIG. 22 more clearly illustrates the pathway of wires 126 and 128 as they traverse from each respective actuator block or handle 114, 115 into the tubular member 112. In use, each actuator block can be pulled proximally or pushed distally to pull or push each wire 126, 128 to effectuate operation of the distal anchor assembly 120 to deploy the fascia anchor when it is in position. FIG. 23 illustrates a lower exploded view wherein wire 126 is received in a channel defined in an underside of block 115b. FIG. 24 illustrates an exploded view of block or actuator handle 114 showing components 114a, 114b separated. Each block 114, 115 sandwiches a respective wire 128, 126 between each of its halves, wherein a groove to receive the wire can be formed into one or both of the halves of each block.

FIGS. 25A-26B are enlarged isometric views of a distal portion of the system of FIG. 14 illustrating aspects of a fascial anchor portion of the system. Anchor assembly 120 is formed from two portions, a first, proximal portion 124 that is attached to the distal end of the tubular member, and a second, distal portion 122 that is removably attached to proximal portion 124 by a pull wire 126. Pull wire 126 traverses passages through both components to hold the components in alignment as they are being advanced through tissue. The components 124, 122 are further held together by a keyed arrangement wherein, when the push or pull rod 126 is in place, the components 122, 124 cannot separate along an axial, lateral or rotational direction. Once the pull rod is withdrawn proximally, components 124, 122 are able to separate, permitting the portion 122 to be left behind in the patient after the fascia has been traversed, with a trailing tether 130 passing through an opening of component 122. FIG. 25B shows relative routing of the tether or suture 130 through component 122, while pull wire 126 holds components 122, 124 together.

Figure 26B:
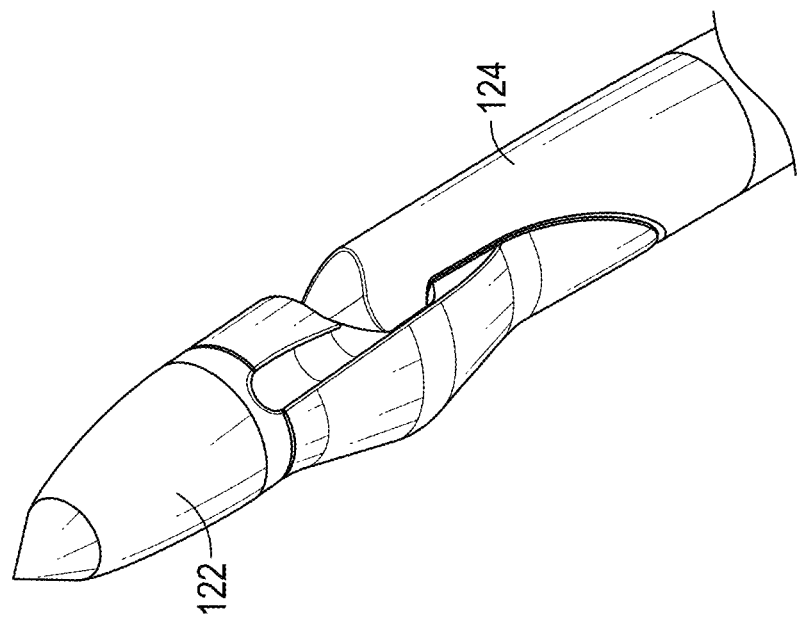
Figure 26A:
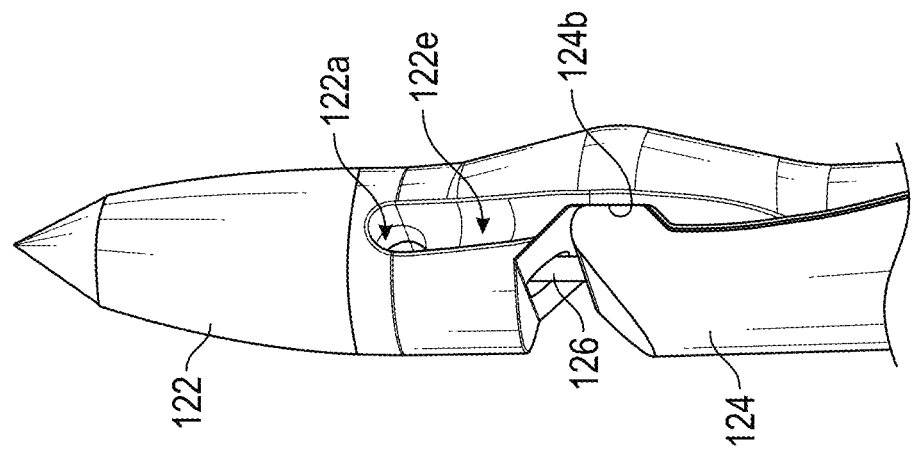

FIGS. 26A-26B illustrate components 122, 124 with the tether or suture 130 removed for purposes of illustration. Distal anchor component 122, which is removable from the system, defines an opening 122a laterally therethrough to permit passage of the suture 130. If desired, a channel 122e can be defined along either side of the anchor portion 122 proximal to opening 122b to permit the suture to be at least partially received therein to lower friction when introducing the assembled device 100 through tissue.

Figure 27A:
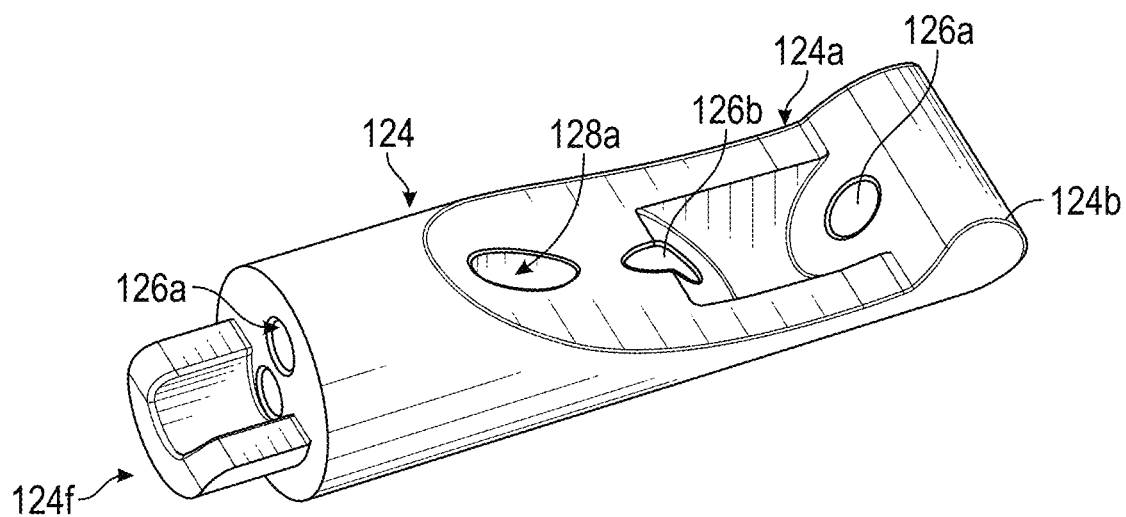
FIGS. 27A-27C are various isometric views of a distal portion of the delivery system of FIG. 14 that couples to the fascia anchor of the system of FIG. 14.
Figure 27B:
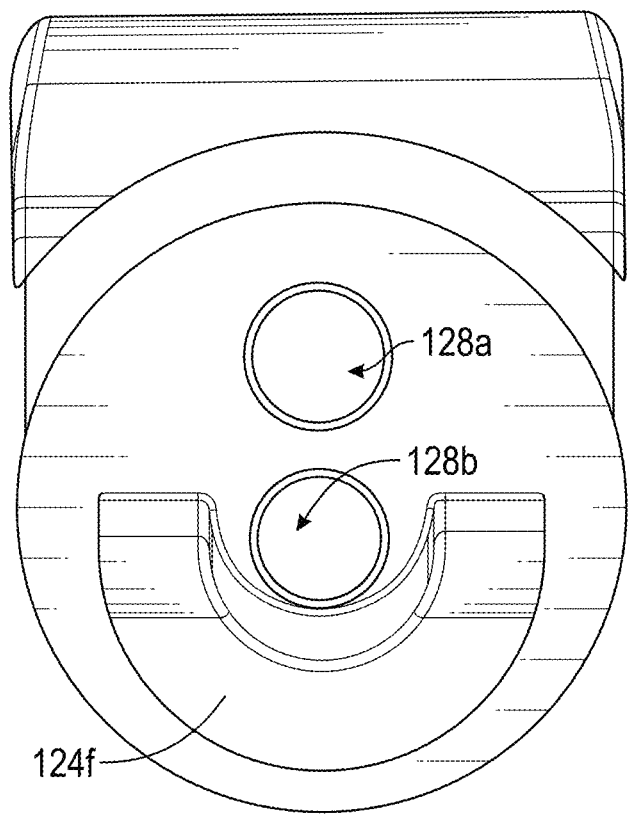
Figure 27C:
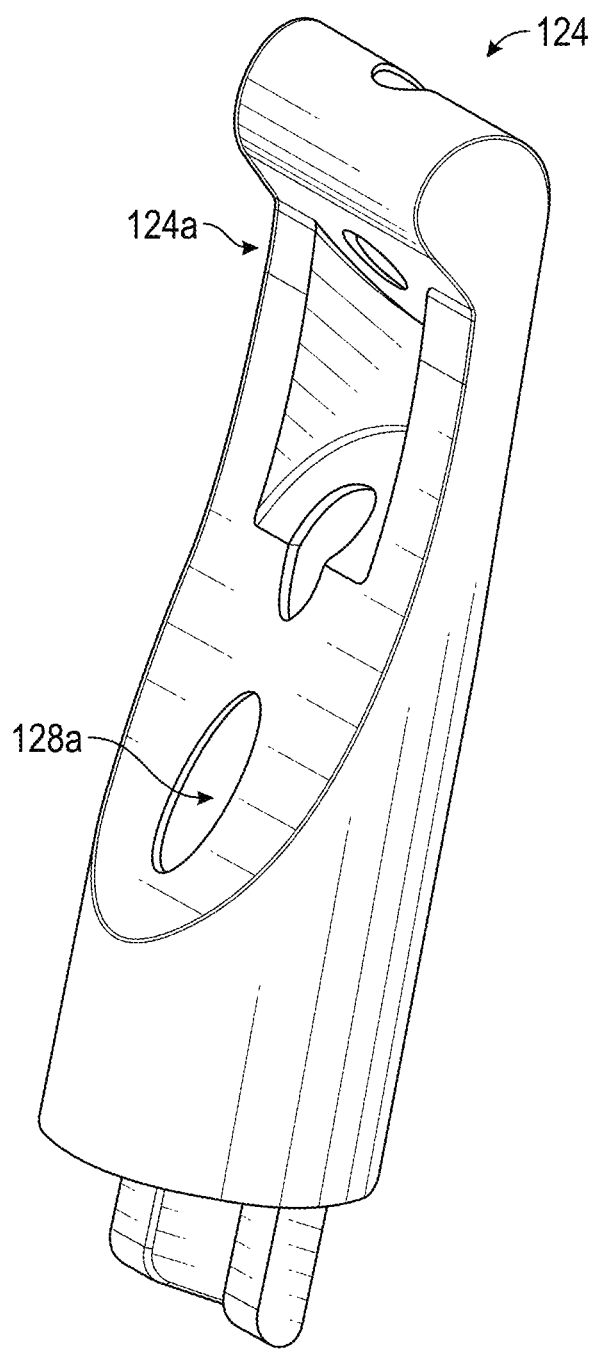

FIGS. 27A-27C are various isometric views of the proximal portion 124 of the anchor assembly 120 that couples to the distal removable section 122 of the anchor assembly. Component 124 includes a proximal end that begins in a crescent shaped sleeve 124f that is received by a lumen of tubular member 112 and coupled thereto by any suitable technique (adhesive, welding, and the like). The main body of component 124 is generally cylindrical and elongate, includes a scalloped or recessed section 124r between its ends, and includes a rounded or fist-shaped, rounded distal end 124b. A first set of elongate axial passages 126b, 126a are defined through section 124 to accommodate the pull wire or tube 126 that holds components 122, 124 together during delivery. These passages permit the pull wire or tube 126 to extend fully through component 124 and into component 122. As second passage 128a is also defined axially through a proximal portion of component 124 and laterally offset from passage 128b. Passage 128a receives a push tube or push rod 128 therethrough to push against a portion of anchor portion 122 to help rotate anchor portion 122 into an orientation that is out of axial alignment with the axial direction of device 100 to place it along an orientation that is oblique or perpendicular to the direction of travel of the suture so that the anchor provides adequate resistance against a tensile force applied to the suture 130.

Figure 28C:
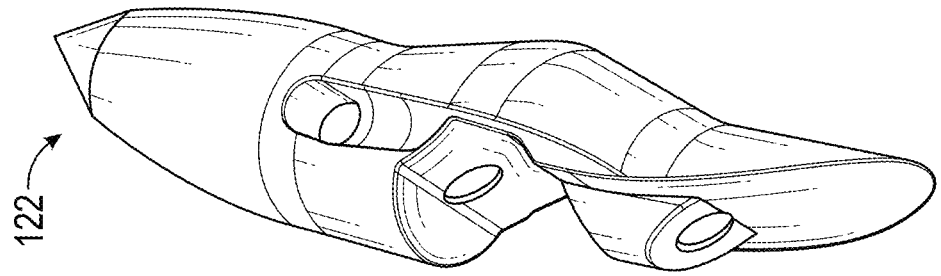
FIGS. 28A-28C are various isometric views of a fascia anchor of the system of FIG. 14.
Figure 28B:
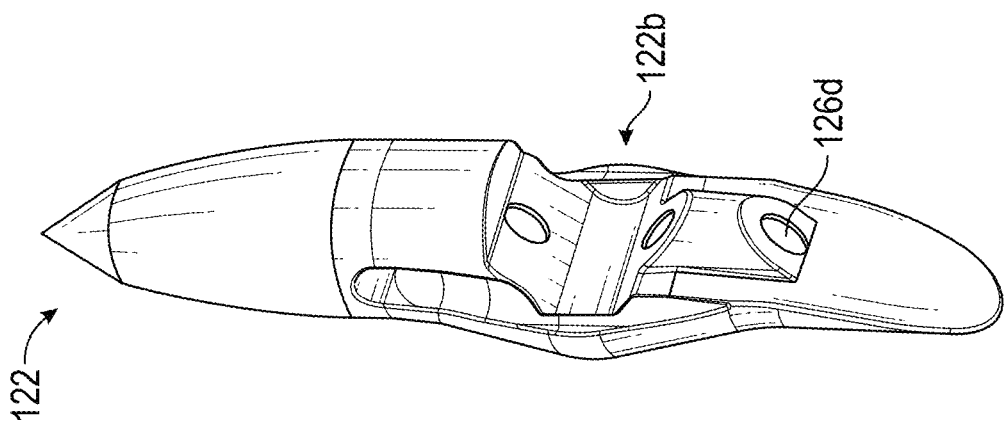
Figure 28A:
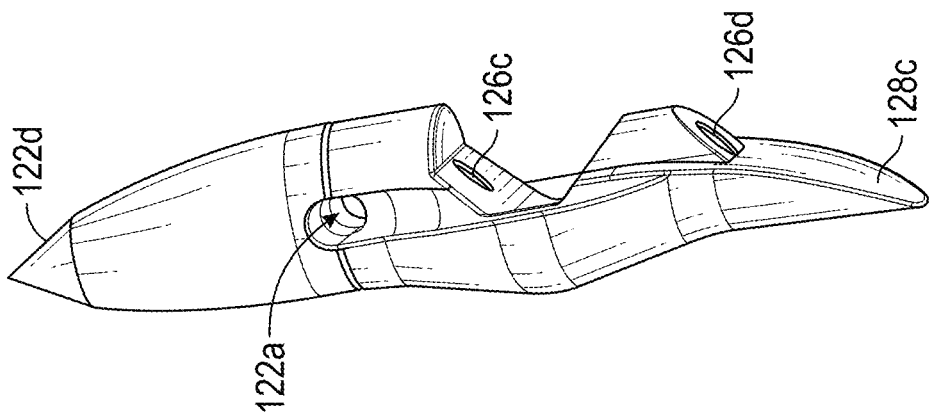

FIGS. 28A-28C are various isometric views of a fascia anchor 122 of the system of FIG. 14. Anchor 122 is the portion of the system left inside the body that is delivered to a point within or beyond the fascia to provide an anchor for the tether 130. Anchor 122 includes a pointed distal end 122d to bluntly dissect tissue when being advanced by the delivery system 100. Passages 126c, 126d receive wire 126 therethrough. First shaped distal end of component 124 is received within recess 122b of distal anchor 122. Thus, when assembled, wire 126 passes through passages 126a, 126b of component 124 and passages 126c, 126d of component 122, providing a strong interlock between components 122, 124. Anchor 122 further defines a push surface or push rod receiving surface 128c that is urged on by distally advancing wire 128 as the cavity 122b of anchor pivots about the first shaped rounded distal end of component 124. As such, in use, the delivery system 100 delivers anchor into or past the fascia as described generally above. But at this point, anchor 122 is still longitudinally aligned with the delivery system 100, and this could lead to the anchor being pulled out when tension is applied to the suture. So, once the anchor 122 is in position, the wire 126 is withdrawn by removing tape 166 (or other retainer) and proximally advancing block 115 that is attached to wire 126. This causes the wire 126 to retreat out of the distal anchor 122, freeing the anchor from the mechanism except for tension applied to the tether or suture 130, which is routed through the opening 122a of component 122. While applying tension to the tether, pushrod or push tube 128 is pushed distally by removing tape 164 from the housing 110, permitting block 114, which is attached to the proximal end of the wire or tube or rod 128, to be advanced distally out through opening 128a, and into surface 128c. The force applied to surface 128c by the distal end of the rod 128, which is applied off of the central axis of the device 100, causes leverage, or a moment, about a point of rotation defined by the cooperative movement of the inner curved surface of cavity 122b about the rounded distal surface of component 124. Continued pushing by the push rod or tube or wire 128 while maintaining tension on the tether 130 to hold the components 122, 124 in contact causes the proximal end of anchor 122 to swing in a distal direction, and the distal end 122d of the anchor to swing proximally until the anchor has obtained an orientation that is oblique, and if possible, orthogonal or perpendicular to the longitudinal axis of the delivery system 100. After this has occurred, the device 100 can be withdrawn from the patient leaving the anchor 122 in place in the fascia with the suture 130 trailing out through the fascia and the passage defined by the insertion of device 100, with both trailing ends of the suture extending through the vaginal wall, and out of the patient's vagina. At this time, the suture 130 is routed through the opening 122a of the anchor 122. At this time, a vaginal anchor, such as 140 or 240, can be introduced over the suture ends 130 using the suture ends as a guide rail. Tension can then be applied to the suture 130 to lift the wall of the vagina, and the vaginal lock can be locked in place. As desired or needed, the vaginal lock can be unlocked and the tension can be adjusted to ensure that urinary leakage is minimized or stopped.

Figure 29B:
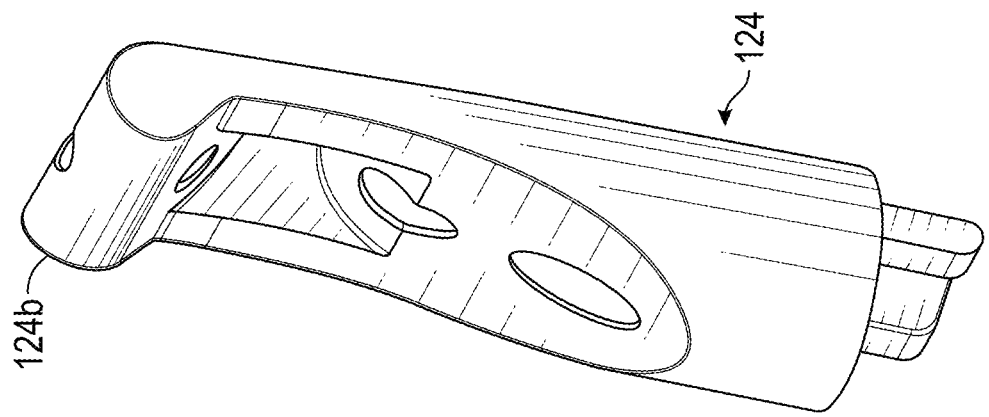
FIGS. 29A-29B are isometric views of the fascia anchor and a distal end portion component of the delivery system of FIG. 14.
Figure 29A:
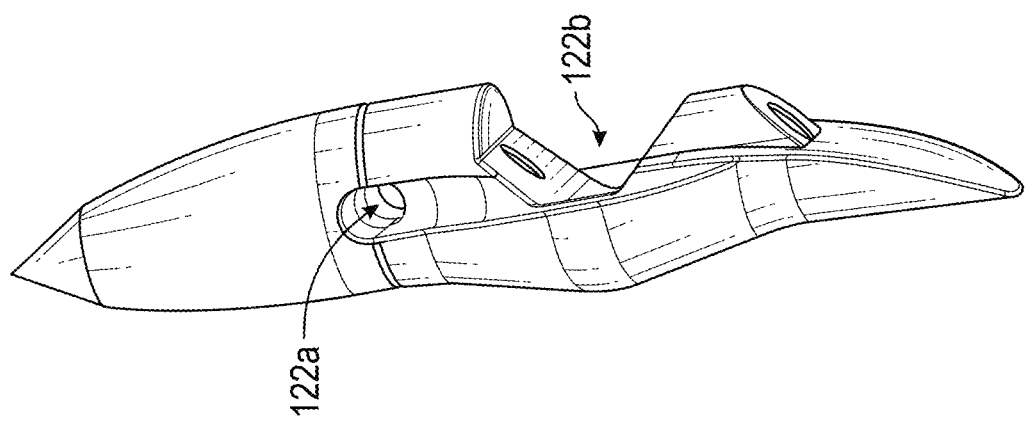
Figure 30:
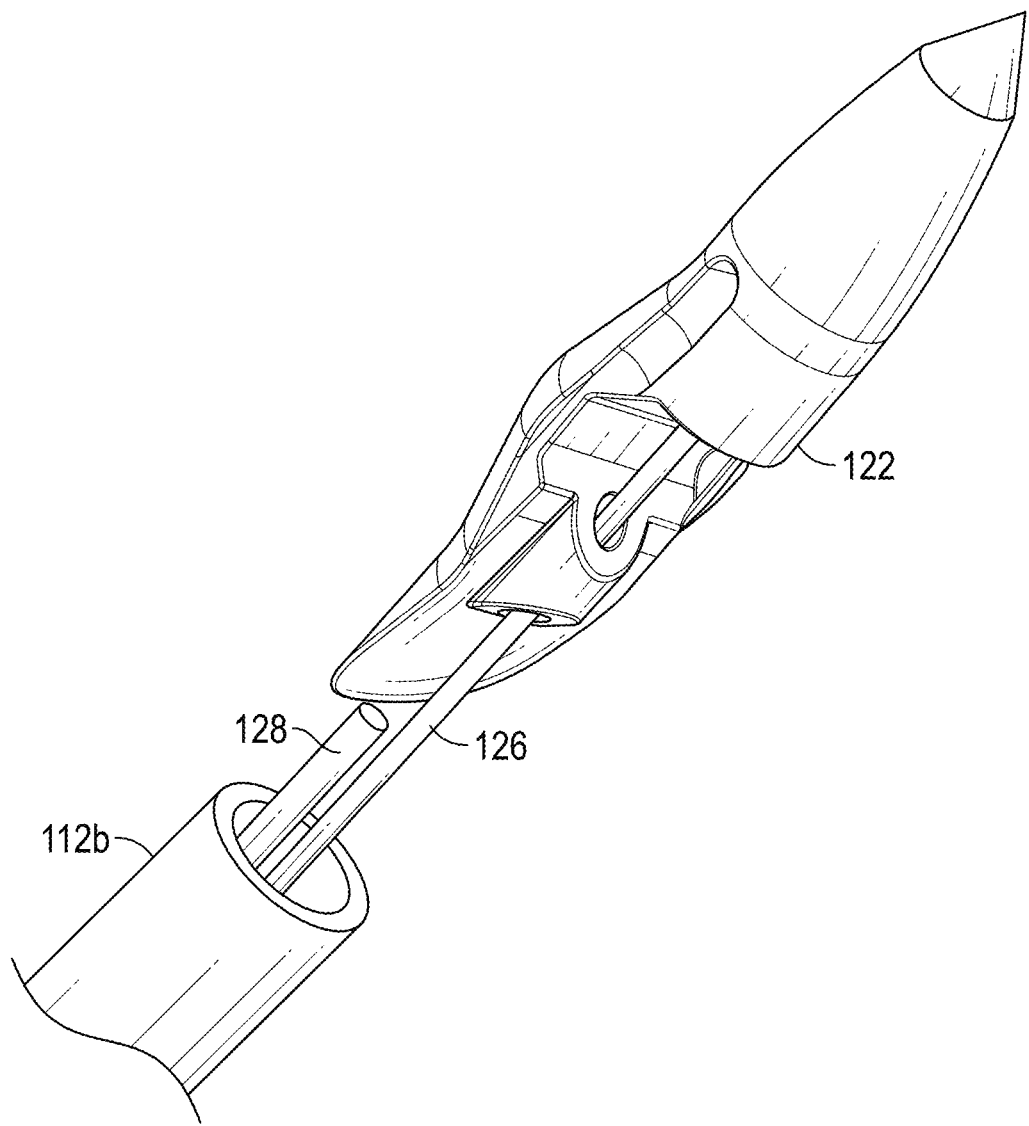
FIG. 30 is an isometric view of a distal portion of the delivery system of FIG. 14 omitting a component of the system to illustrate relative placement of a retainer rod and a push rod to urge the fascia anchor into position.

FIGS. 29A-29B are isometric views of the fascia anchor and a distal end portion component of the delivery system of FIG. 14. In this figure it can be seen how the rounded distal end 124b of component 124 interfits with recess 122b of component 122. FIG. 30 is an isometric view of a distal portion of the delivery system of FIG. 14 omitting a component 124 of the system 100 to illustrate relative placement of a retainer rod 126 and a push rod 128 to urge the fascia anchor 122 into position.

Figure 31:
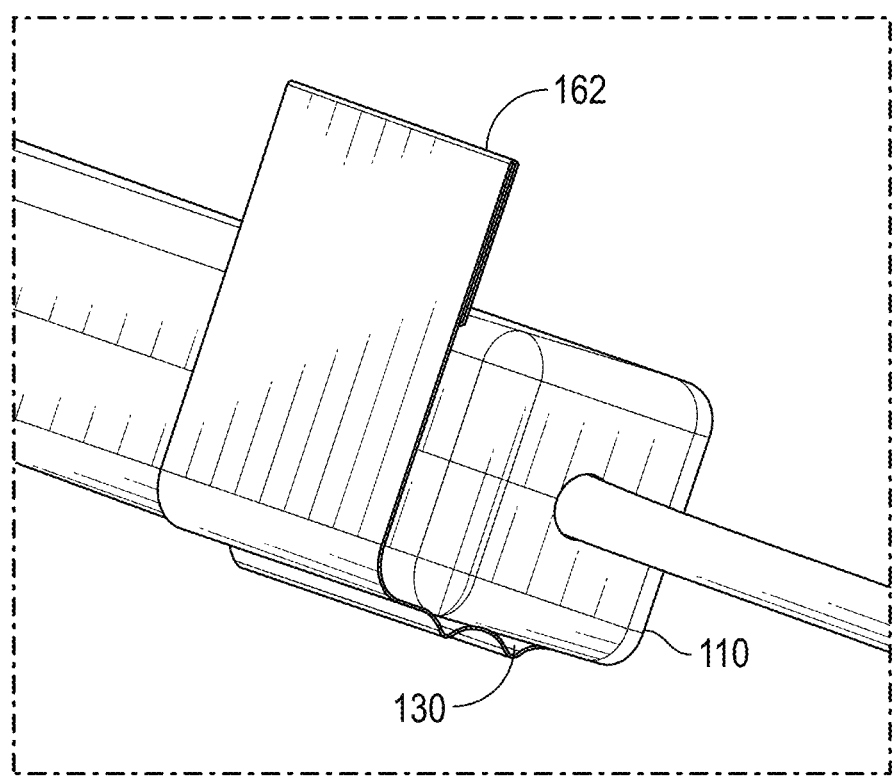
FIG. 31 is a closeup view of a distal end portion of a handle portion of the delivery system of FIG. 14.
Figure 32:
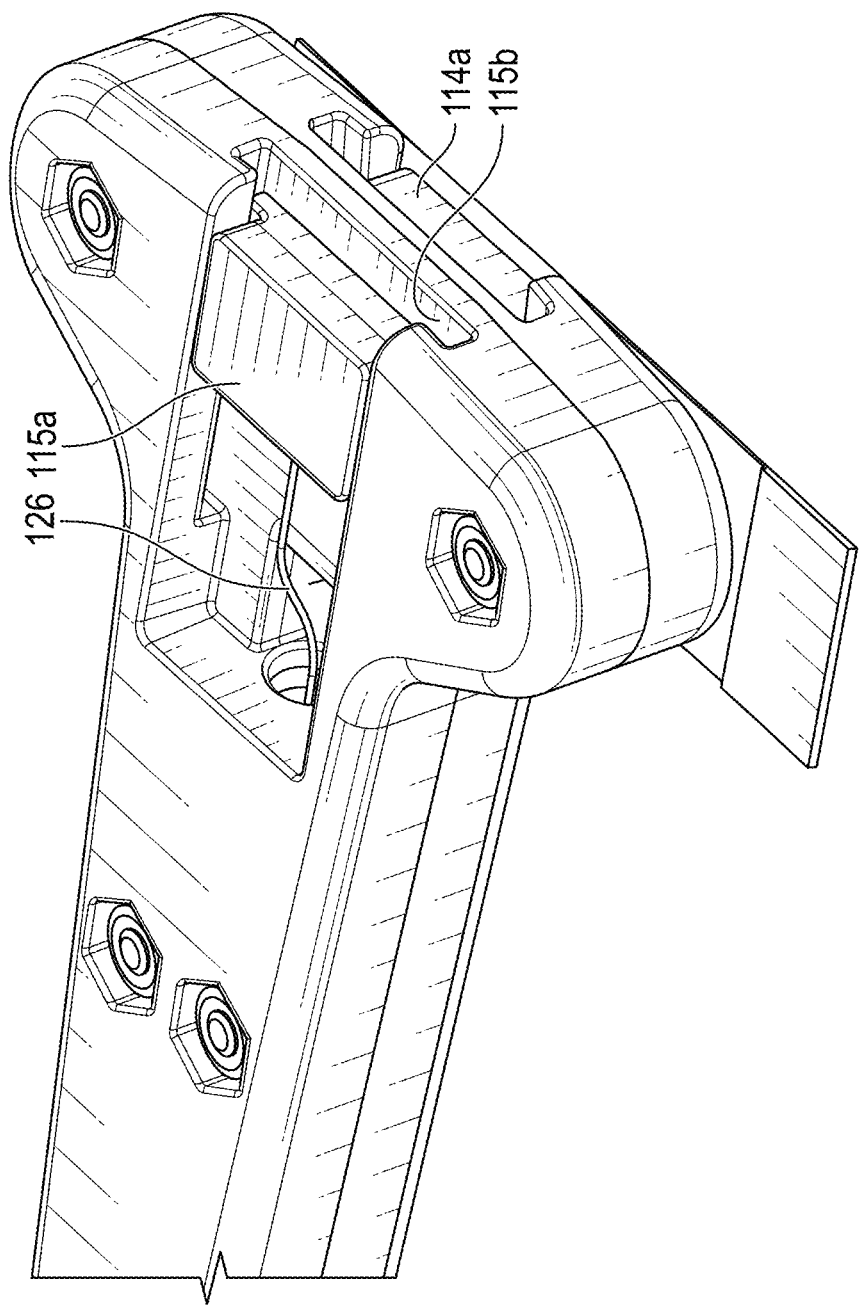
FIG. 32-35 are closeup isometric views of a proximal end portion of a handle portion of the delivery system of FIG. 14.
Figure 33:
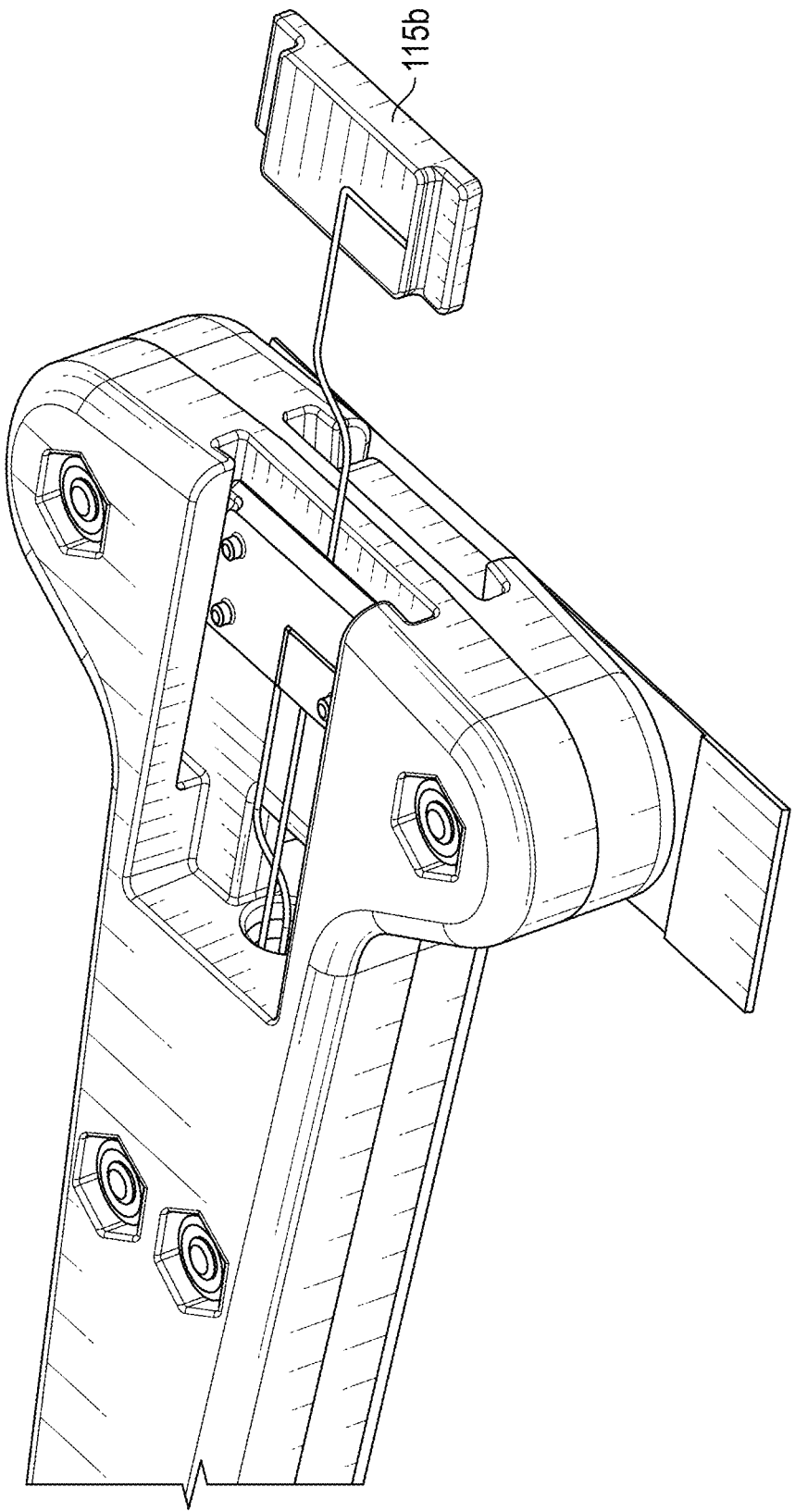
Figure 34:
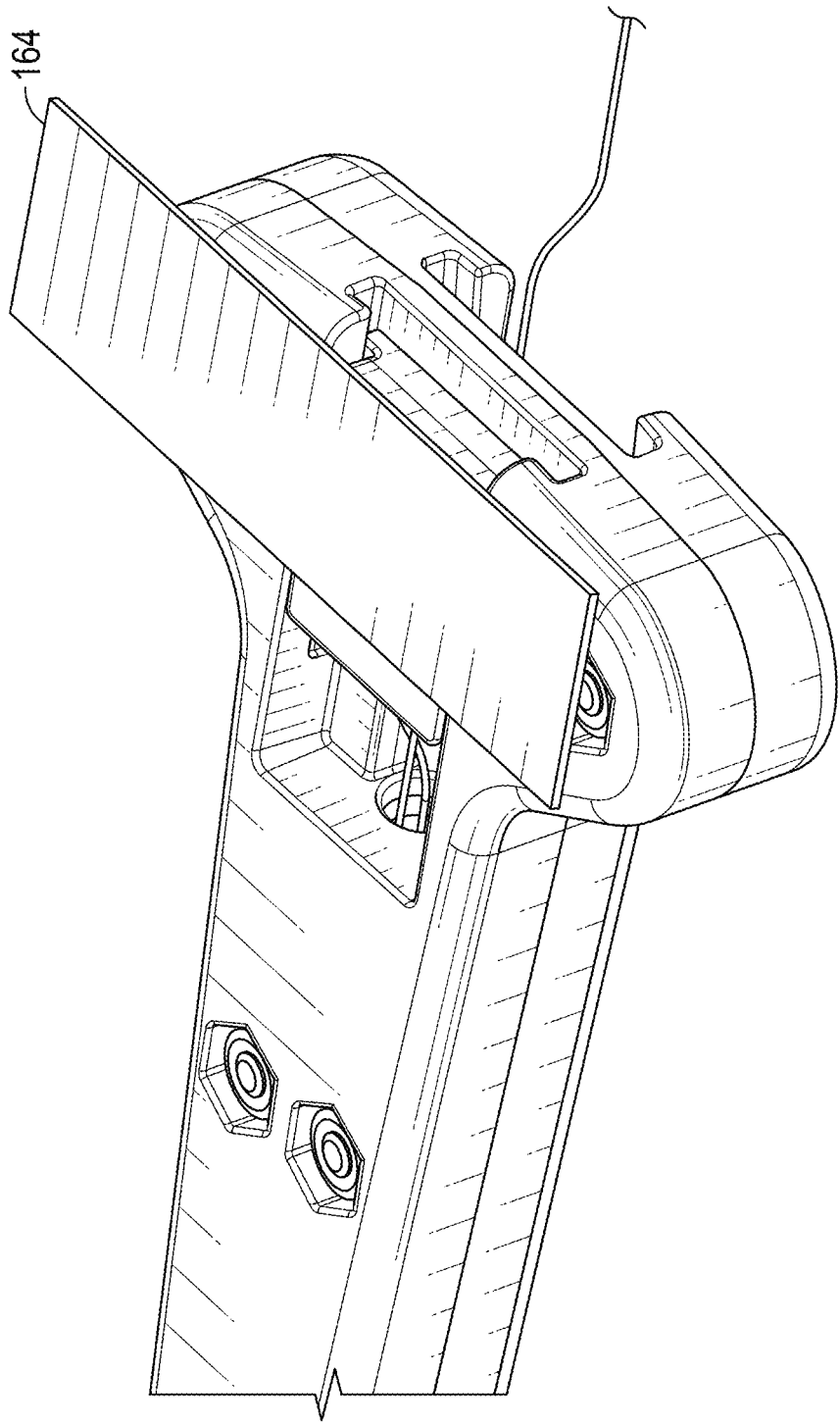
Figure 35:
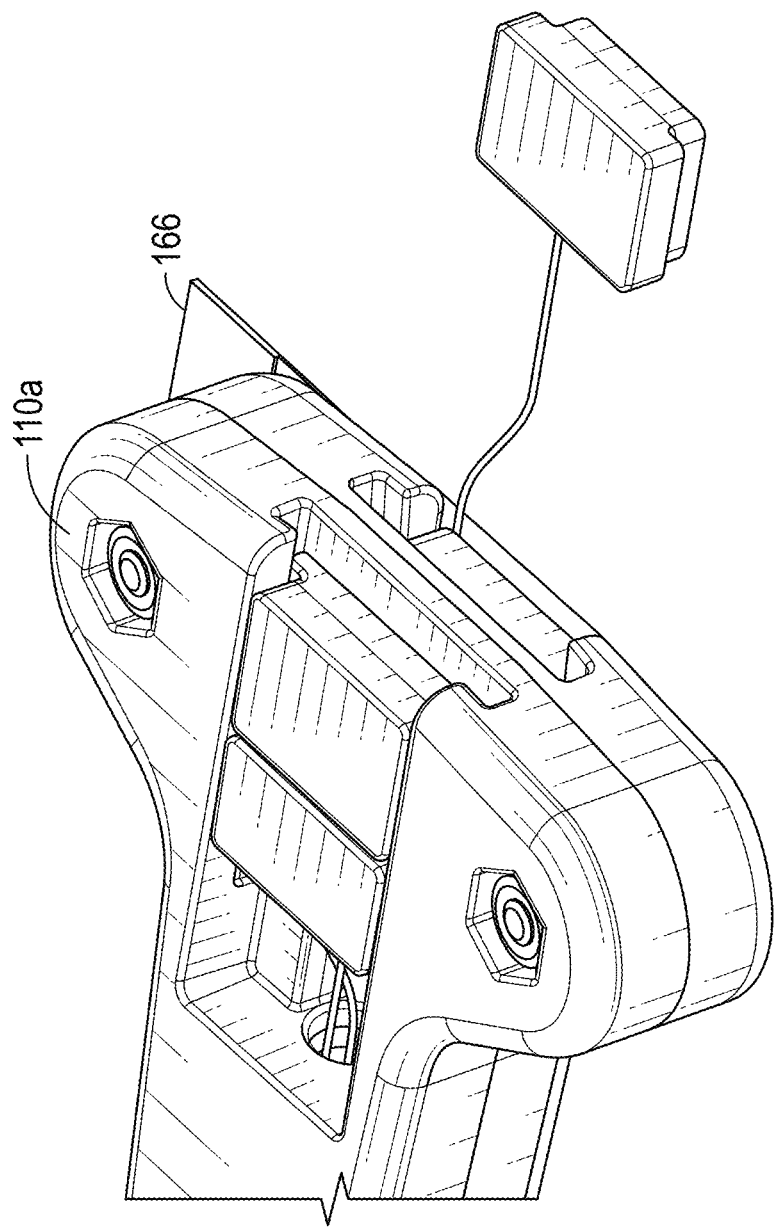
Figure 37:
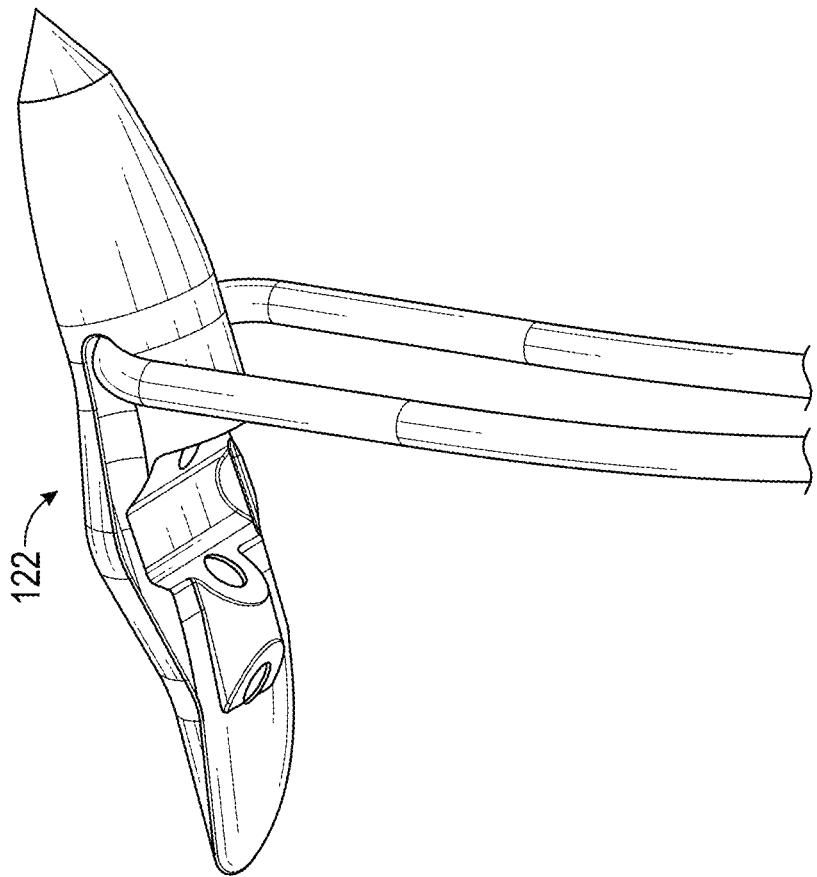
FIGS. 36-37 are isometric views of the fascia anchor of FIG. 14 showing relative placement of a suture passing therethrough.
Figure 36:
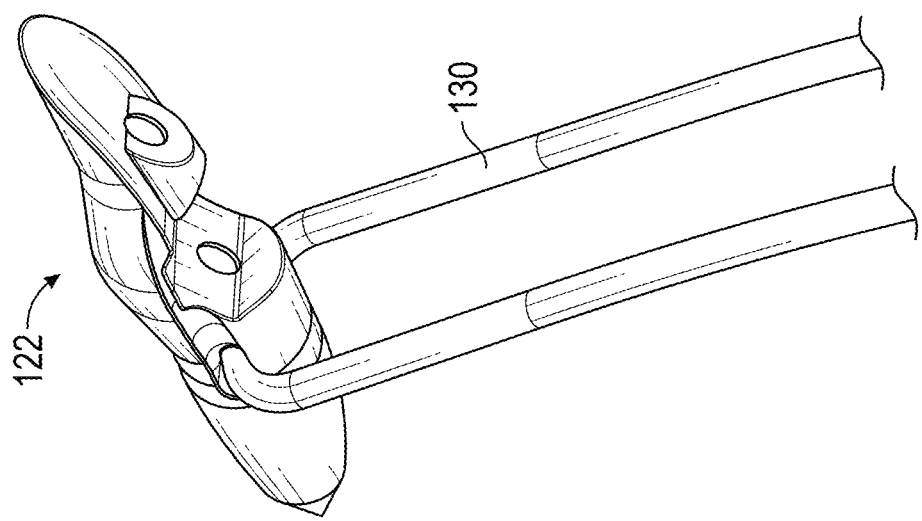
Figure 40:
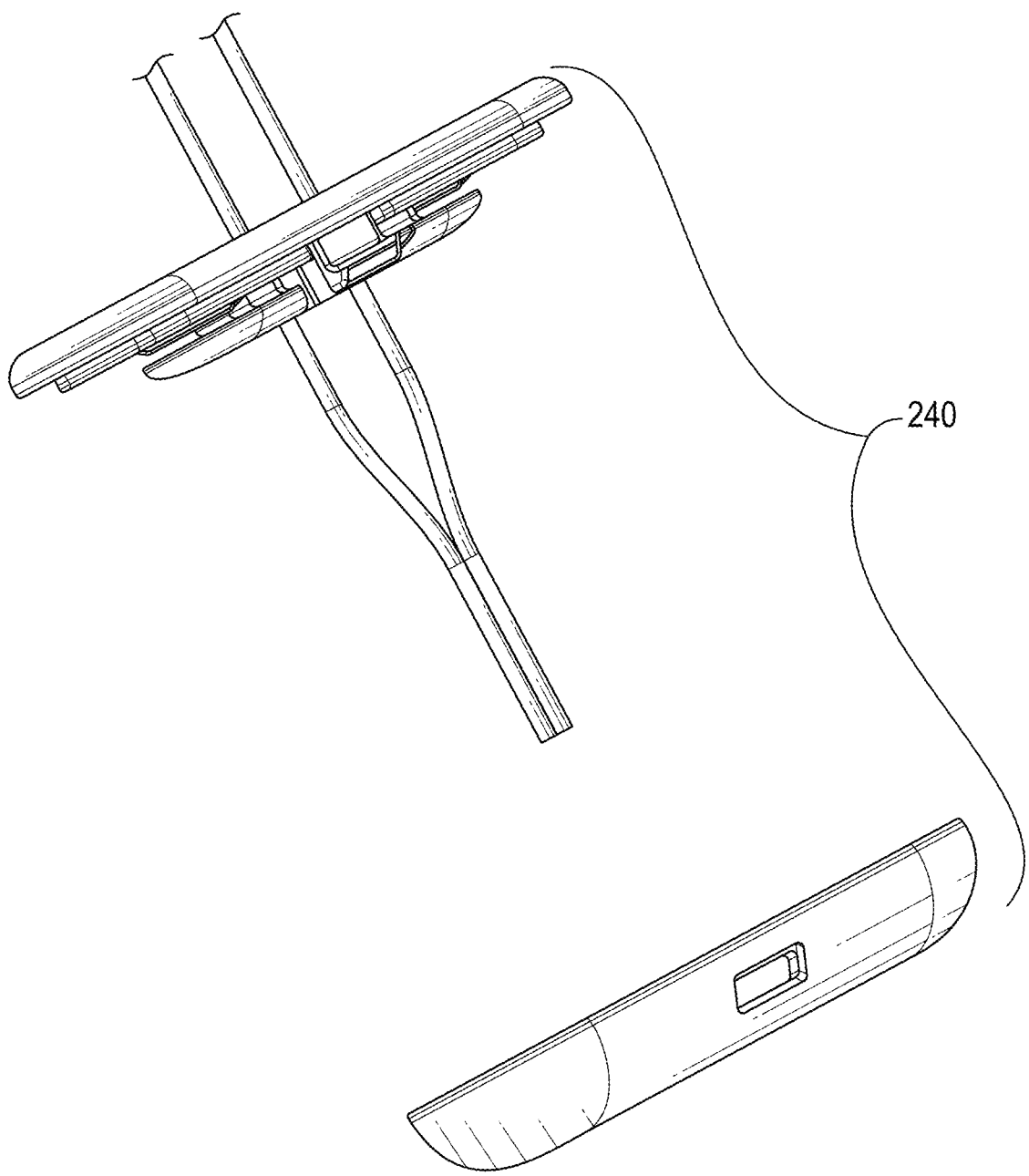
FIGS. 40-44B are various isometric views of a further implementation of a vaginal anchor in accordance with the present disclosure.
Figure 41:
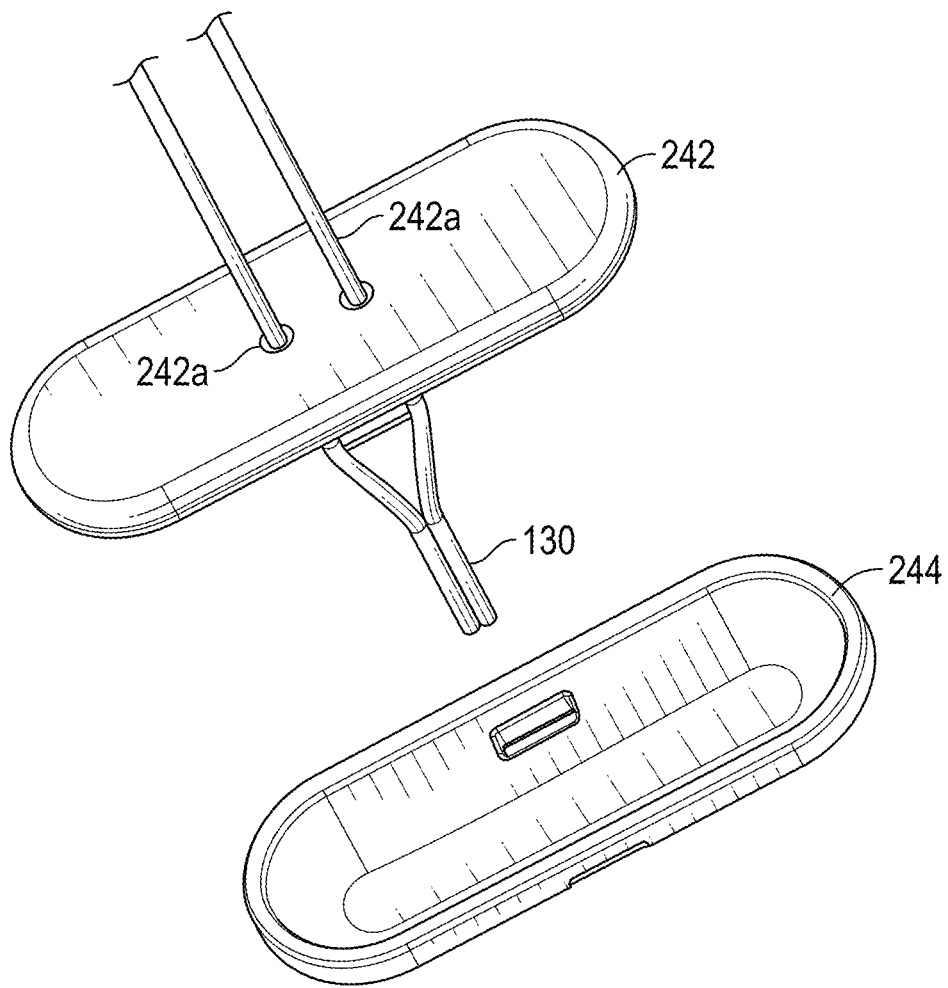

FIG. 31 is a closeup view of a distal end portion of a handle portion of the delivery system of FIG. 14, illustrating relative placement of tape or retainer 162 to hold suture 130 in place where indicated. FIG. 32-35 are closeup isometric views of a proximal end portion of a handle portion 110 of the delivery system of FIG. 14. In this view, the actuator block 115 coupled to pull wire 126 is shown both in the track, as well as out of track, for purposes of illustration only. If desired, additional actuator blocks could be provided (e.g., two in each channel 113a, 113b) to provide means for pulling or pushing additional actuator wires or rods, as desired. FIGS. 36-37 are isometric views of the fascia anchor of FIG. 14 showing relative placement of a suture passing therethrough. As can be seen, in this orientation, the longitudinal axis of the anchor 122, once rotated, is orthogonal to the suture 130, or nearly so, to maximize pull out resistance. FIGS. 38-39 are isometric views of portions of the system of FIG. 14, showing relative placement of retainer plates 117b around tubular member 112. FIG. 39 illustrates the manner in which tubular member 112 terminates in components 124.

Figure 42:
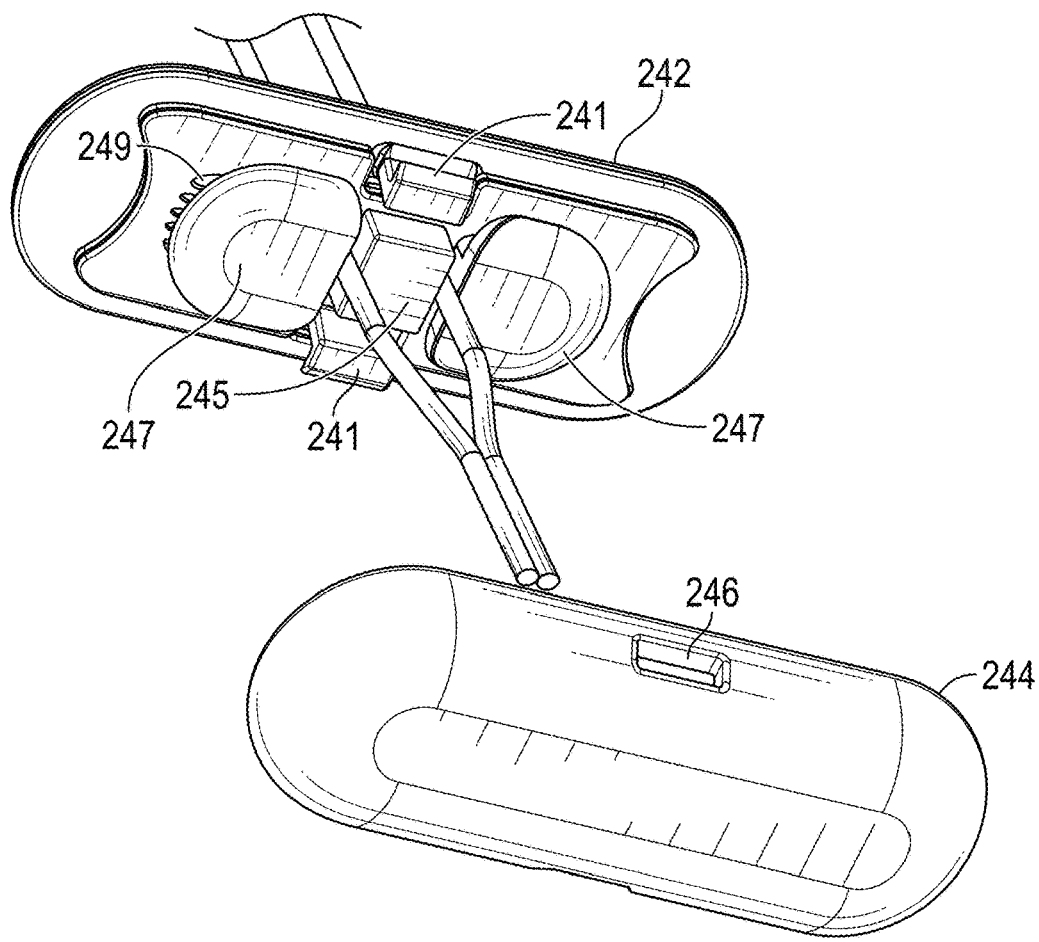
Figure 43:
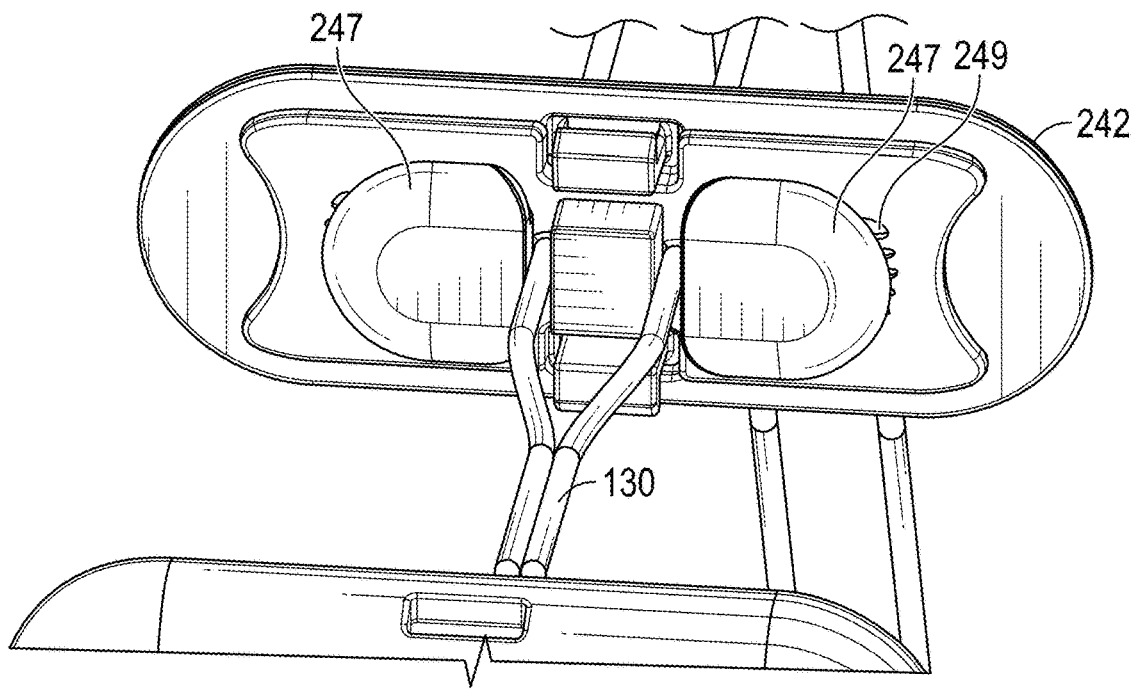
Figure 44A:
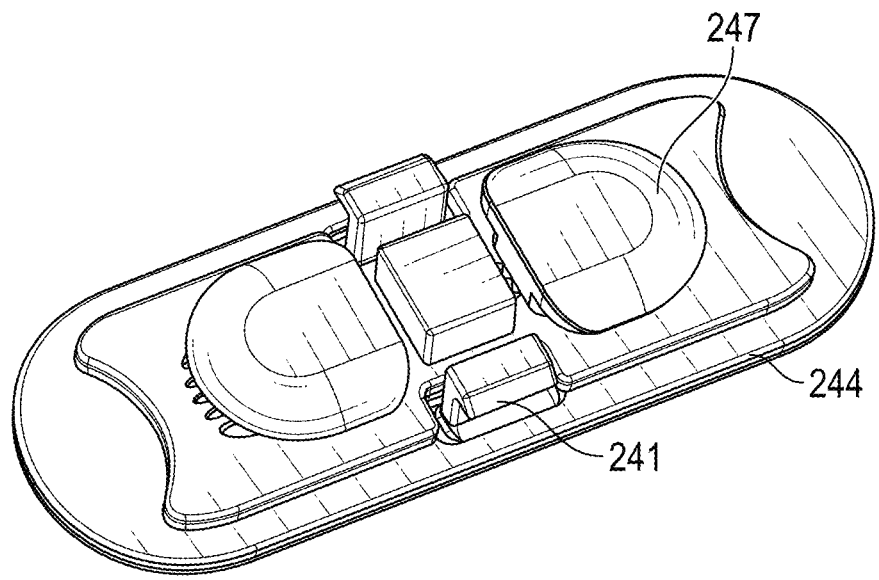
Figure 44B:
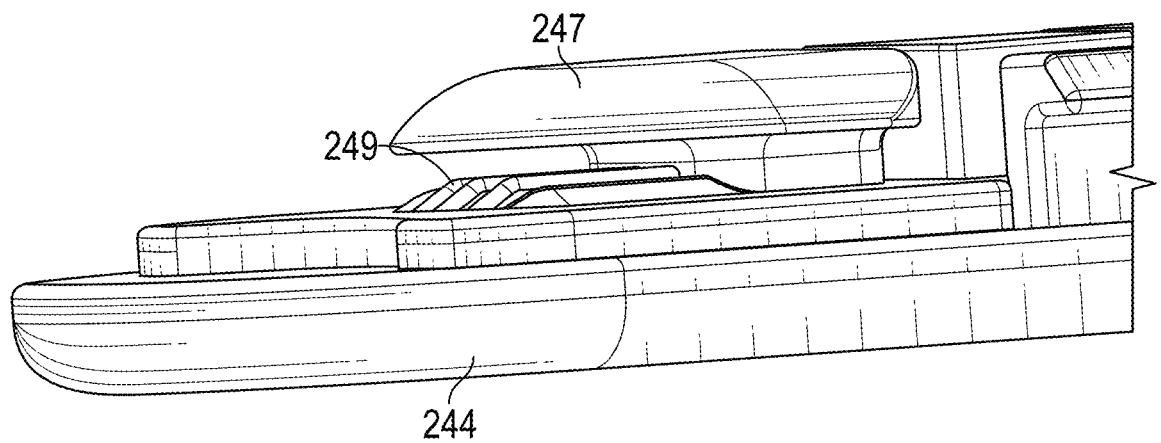

FIGS. 40-44B are various isometric views of a further implementation of a vaginal anchor 240 in accordance with the present disclosure. Anchor 240 is oblong and is defined by an atraumatic outer surface that lacks sharp edges. As depicted, anchor 240 is composed of an upper portion 242, and a lower portion, or cap, 244. Portions 242 and 244 cooperate to define an enclosure. Upper portion 242 defines two openings therethrough to accommodate passage of sutures 242a therethrough. As depicted in FIG. 42-44, upper portion 242 of the lock, which lays against the vaginal wall after implantation, includes a central boss 245 with a fastening cleat disposed on each side thereof. Each fastening cleat includes a plate displaced from a surface of the upper portion 242 that defines a gap between the plate and the surface. Each gap includes one or more ribs or ridges 249 to hold a suture 130 in place by way of an interference fit. In use, the tethers 130 are wrapped around each cleat after tensioning, and cover 244 is then coupled to portion 242, holding the trailing suture inside of the anchor. The upper portion 242 of the anchor 240 includes one or more barbs 241 disposed on a cantilevered arm that is received by a respective opening 246 in the lower portion 244. As with other anchors discussed herein, after installation, the cover 244 can be removed, and tension in the tether 130 can be adjusted by unwinding the tether from each cleat 247, adjusting tension in the tether, and re-anchoring the tether around the cleat.

Figure 45:
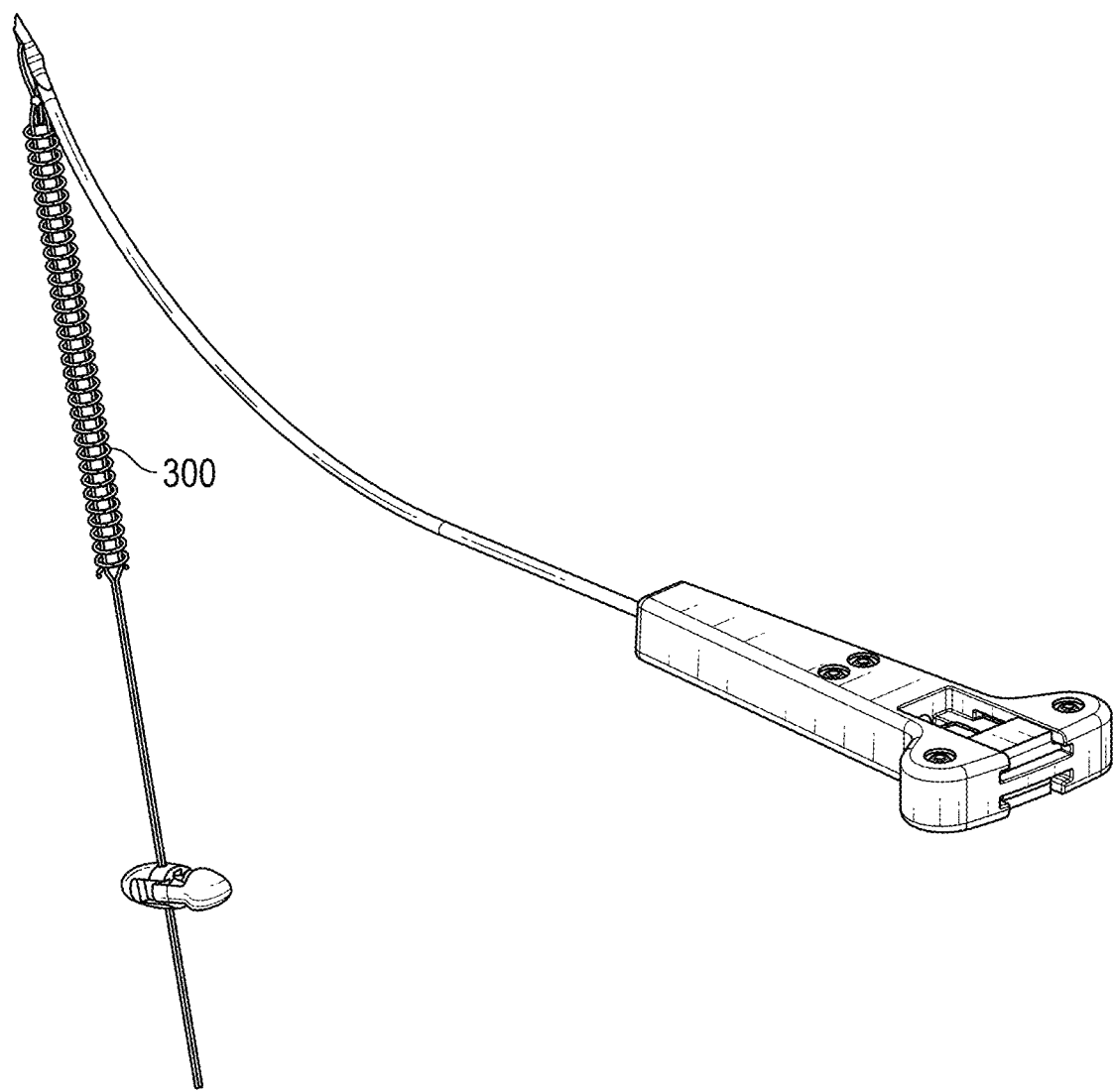
FIG. 45 is a representative illustration of an implementation of using a scar forming matrix material to enhance the formation of scar tissue to help ensure long term benefits from a procedure as described herein.

In accordance with further aspects, the system can be configured to encourage scar tissue to form in order to maintain the new geometry provided by the procedure. For example, one or more of the fascia anchor, tether(s) and vaginal anchor can be provided with a surface or projections that cause scar tissue to form. For purposes of illustration, and not limitation, a representative implementation of such an arrangement can be found in FIG. 45 wherein matrix materials 300, such as in the form of spirals, helices, lattices, matrices and/or protrusions are attached to the tethers 130. If attached to or molded integrally with the tethers, the matrix material 300 can be pulled into the tissue with the fascia anchor and tethers 130. Alternatively, such matrix material could be introduced in a separate operation from the tethers 130. The matrix material 300 can be absorbable or not be absorbable as desired. Enhanced scarring along the length of the tether where it passes through tissue can enhance the strength of the tissue structure that is caused by the procedure. The matrix material can be natural material and/or synthetic material. The tethers and/or matrix material can be formed in separate operations or the same operation from absorbable or non-absorbable material. In some implementations, the material can include PDS, as described herein, and/or variations of Poly (lactic acid) such as PLA, PDLA (Poly D Lactic Acid), or PLLA (Poly L Lactic Acid) of various molecular weights and densities. For example, the suture material and matrix material can be formed in the same set of molding and/or extrusion operations. In other implementations, the matrix material 300 can be made from animal skin such as fish skin, and the like. The matrix material preferably extends from a location proximate the fascial anchor 122 for a distance of about two to about five centimeters, but not the full distance to the vaginal anchor. Preferably, the matrix material 300 forms a mass of material in the region of the tethers 130 to induce formation of scar tissue to hold the urethra in place after the procedure.

The methods and devices provided by the present disclosure, as described above and shown in the drawings, provide for methods and systems for medical diagnosis and treatment with superior properties as described herein. It will be appreciated that the disclosed system, or portions thereof, can be used for other applications. It will be apparent to those skilled in the art that various modifications and variations can be made in the embodiments of the present disclosure described herein without departing from the spirit or scope of the disclosure. Thus, it is intended that the present disclosure include modifications and variations that are within the scope of the appended claims and their equivalents.

What is claimed is:

1. A system to treat stress urinary incontinence (SUI), comprising:
a housing;
an elongate shaft extending distally from the housing, the elongate shaft defining a first elongate passage therethrough along at least a portion of the length of the elongate shaft;
a tissue anchor removably disposed at a distal end of the elongate shaft, the tissue anchor defining a second elongate passage therethrough that is coaxial with the first elongate passage;
a tether coupled to the tissue anchor;
a removable rod or wire disposed through the first elongate passage and the second elongate passage, wherein the removable rod or wire, the tissue anchor and the elongate shaft are configured to prevent longitudinal and lateral movement of the tissue anchor with respect to the elongate shaft while the removable rod or wire is disposed in the first elongate passage and the second elongate passage
wherein, upon the removable rod or wire being withdrawn proximally out of the second elongate passage, the tissue anchor is released from the elongate shaft to permit the elongate shaft to be removed from a patient's tissue while leaving the tissue anchor behind with the tether extending from the tissue anchor along a path through tissue previously occupied by the elongate shaft.

2. The system of claim 1, wherein the tether passes over a first bearing surface defined by the tissue anchor.

3. The system of claim 2, wherein first and second ends of the tether are coupled to the housing.

4. The system of claim 2, wherein the tissue anchor further defines a longitudinal indentation on opposing lateral sides of the tissue anchor to at least partially receive a respective portion of the tether therein.

5. The system of claim 1, further comprising a vaginal anchor configured to couple to the tether, wherein the vaginal anchor is configured to couple to the tether after tension has been applied to the tether after the tissue anchor has been implanted.

6. The system of claim 5, wherein the vaginal anchor includes at least one cleat to couple to the tether.

7. The system of claim 5, wherein the vaginal anchor includes at least two housing components that couple with each other.

8. The system of claim 7, wherein the at least two housing components clamp against the tether while the at least two housing components are coupled together.

9. The system of claim 8, wherein the two housing components couple to each other in a plurality of discrete relative positions.

10. The system of claim 8, wherein the tether traverses a tortuous route through the vaginal anchor while the at least two housing components are coupled together.

11. The system of claim 5, wherein at least one of the tissue anchor, the vaginal anchor and the tether is formed from bioresorbable material.

12. The system of claim 5, wherein the vaginal anchor is defined by a smooth and oblong surface.

13. The system of claim 5, wherein the vaginal anchor defines at least one ramped surface therein to clamp the tether in place while the vaginal anchor is in a locked condition.

14. The system of claim 1, wherein at least one of the tissue anchor and a distal end region of the elongate shaft defines a laterally oriented protrusion configured to be received by a laterally oriented indentation of the other of the tissue anchor and the distal end region of the elongate shaft.

15. A system to treat stress urinary incontinence (SUI), comprising:

a housing including at least one actuator;

an elongate shaft extending distally from the housing;

a tissue anchor removably disposed at a distal end of the elongate shaft;

a tether coupled to the tissue anchor;

wherein, upon the at least one actuator being actuated, the tissue anchor is released from the elongate shaft to permit the elongate shaft to be removed from a patient's tissue while leaving the tissue anchor behind with the tether extending from the tissue anchor along a path through tissue previously occupied by the elongate shaft;

and further wherein a distal end surface of the elongate shaft defines a first laterally oriented curved surface configured to be received by a corresponding second laterally oriented curved surface defined in a portion of the tissue anchor permitting the tissue anchor to rotate about the distal end surface of the elongate shaft while the relative position of the elongate shaft and tissue anchor are unconstrained.

16. The system of claim 15, wherein the first laterally oriented curved surface is a convex surface and the second laterally oriented curved surface is a concave surface.

17. The system of claim 15, wherein the system further defines a longitudinal lumen along a length thereof from the housing to the tissue anchor to slidably receive a pull wire therein.

* * * * *